US012160609B2

(12) United States Patent
Foley et al.

(10) Patent No.: US 12,160,609 B2
(45) Date of Patent: Dec. 3, 2024

(54) SEGMENT-WISE PREDICTION MACHINE LEARNING FRAMEWORKS

(71) Applicant: Optum Services (Ireland) Limited, Dublin (IE)

(72) Inventors: Colum Foley, Dublin (IE); Paul Ferguson, Dublin (IE)

(73) Assignee: Optum Services (Ireland) Limited, Dublin (IE)

( * ) Notice: Subject to any disclaimer, the term of this patent is extended or adjusted under 35 U.S.C. 154(b) by 168 days.

(21) Appl. No.: 17/805,340

(22) Filed: Jun. 3, 2022

(65) Prior Publication Data
US 2023/0224493 A1 Jul. 13, 2023

Related U.S. Application Data

(60) Provisional application No. 63/266,682, filed on Jan. 12, 2022.

(51) Int. Cl.
*H04N 19/597* (2014.01)
*G06N 20/00* (2019.01)
(Continued)

(52) U.S. Cl.
CPC ........... *H04N 19/597* (2014.11); *G06N 20/00* (2019.01); *H04N 19/17* (2014.11); *H04N 19/503* (2014.11)

(58) Field of Classification Search
CPC .... H04N 19/597; H04N 19/503; H04N 19/17; G06N 20/00; G06N 3/10; G06N 3/048;
(Continued)

(56) References Cited

U.S. PATENT DOCUMENTS 10,102,340 B2 10/2018 Tanner, Jr. et al.
10,319,468 B2 6/2019 Ginsburg
(Continued)

FOREIGN PATENT DOCUMENTS

CN 108334935 A * 7/2018 .......... G06N 3/0454
CN 109636061 A * 4/2019 .......... G06N 3/0454
(Continued)

OTHER PUBLICATIONS

Jain, Ankit. "Claim Analysis and Fraud Detection Using Business Intelligence|Blog," Nalashaa, Feb. 2, 2017, (3 pages), [Retrieved from the Internet Oct. 7, 2022] <URL: https://www.nalashaa.com/claim-analysis-fraud-detection-business-intelligence/.
(Continued)

*Primary Examiner* — Jerry T Jean Baptiste
*Assistant Examiner* — Astewaye Gettu Zewede
(74) *Attorney, Agent, or Firm* — Alston & Bird LLP

(57) ABSTRACT

Various embodiments of the present disclosure provide a segment-wise prediction machine learning framework. In one example, an embodiment provides for generating, using a segment-wise prediction machine learning framework, and based at least in part on a document segment for an input segment and a respective predictive code for the input segment, a segment-wise prediction score for the input segment. The segment-wise prediction machine learning framework may comprise a text embedding machine learning model and may be configured to generate a segment-wise prediction score for the input segment based at least in part on a document embedding for the input segment and a code embedding for the respective predictive code for the input segment. Additionally, the text embedding machine learning model may be trained as part of a code prediction machine learning model that is configured to generate, for a
(Continued)

particular input document data object, a selected code subset.

20 Claims, 13 Drawing Sheets

(51) Int. Cl.
  *H04N 19/17* (2014.01)
  *H04N 19/503* (2014.01)

(58) Field of Classification Search
  CPC .... G06N 3/082; G06N 3/0464; G06N 3/0985; G16H 10/60; G16H 40/20; G16H 50/20
  See application file for complete search history.

(56) References Cited

U.S. PATENT DOCUMENTS

| | | | |
|---|---|---|---|
| 10,552,576 | B2 | 2/2020 | Campbell |
| 11,049,594 | B2 | 6/2021 | Chintamaneni et al. |
| 11,361,381 | B1 | 6/2022 | Lehmuth et al. |
| 2011/0258054 | A1 | 10/2011 | Pandey et al. |
| 2013/0006655 | A1 | 1/2013 | Van Arkel et al. |
| 2013/0054259 | A1 | 2/2013 | Wojtusiak et al. |
| 2014/0081652 | A1 | 3/2014 | Klindworth |
| 2016/0239617 | A1 | 8/2016 | Farooq et al. |
| 2016/0253461 | A1 | 9/2016 | Sohr et al. |
| 2017/0017760 | A1 | 1/2017 | Freese et al. |
| 2017/0322930 | A1 | 11/2017 | Drew |
| 2019/0034589 | A1 | 1/2019 | Chen et al. |
| 2020/0013124 | A1 | 1/2020 | Obee et al. |
| 2020/0104731 | A1 | 4/2020 | Oliner et al. |
| 2020/0311601 | A1* | 10/2020 | Robinson .............. G06N 3/042 |
| 2020/0381090 | A1 | 12/2020 | Apostolova et al. |
| 2021/0056113 | A1 | 2/2021 | Mac et al. |
| 2021/0109915 | A1 | 4/2021 | Godden et al. |
| 2021/0304749 | A1 | 9/2021 | Singh et al. |
| 2021/0313022 | A1 | 10/2021 | Chaballout |
| 2022/0012611 | A1 | 1/2022 | Moradi et al. |
| 2022/0309592 | A1 | 9/2022 | Zahora et al. |
| 2022/0392048 | A1 | 12/2022 | Henry et al. |
| 2023/0048097 | A1 | 2/2023 | Clausen et al. |
| 2023/0101817 | A1 | 3/2023 | Sinha et al. |
| 2023/0131694 | A1 | 4/2023 | Saber et al. |
| 2023/0195443 | A1 | 6/2023 | Eberlein et al. |
| 2023/0385705 | A1 | 11/2023 | Takehara et al. |
| 2024/0078245 | A1 | 3/2024 | Foley et al. |
| 2024/0078609 | A1 | 3/2024 | Foley et al. |
| 2024/0078610 | A1 | 3/2024 | Foley et al. |

FOREIGN PATENT DOCUMENTS

| | | | |
|---|---|---|---|
| CN | 116070630 A | * | 5/2023 |
| WO | 2022/057057 A1 | | 3/2022 |

OTHER PUBLICATIONS

Sowah, Robert A. et al. "Decision Support System (DSS) for Fraud Detection in Health Insurance Claims Using Genetic Support Vector Machines (GSVMs)," Hindawi Journal of Engineering, vol. 2019, Article ID 1432597, pp. 1-19, Sep. 2, 2019, DOI: 10.1155/2019/1432597.

NonFinal Office Action for U.S. Appl. No. 18/153,602, dated Dec. 20, 2023, (12 pages), United States Patent and Trademark Office, US.

Kim, Byung-Hak et al. "Deep Claim: Payer Response Prediction From Claims Data With Deep Learning," arXiv preprint arXiv:2007.06229v1 [cs.LG], Jul. 13, 2020, (9 pages).

Sun, Xu et al. "Feature-Frequency-Adaptive On-Line Training For Fast and Accurate Natural Language Processing," Computational Linguistics, vol. 40, No. 3, Sep. 1, 2014, pp. 563-586, DOI: 10.1162/COLI_a_00193.

Thesmar, David et al. "Combining The Power Of Artificial Intelligence With The Richness Of Healthcare Claims Data: Opportunities and Challenges," PharmacoEconomics, vol. 37, pp. 745-752, Mar. 8, 2019.

Non-Final Rejection Mailed on Feb. 28, 2024 for U.S. Appl. No. 18/153,624, 5 page(s).

Advisory Action (PTOL-303) Mailed on Aug. 20, 2024 for U.S. Appl. No. 18/153,602, 3 page(s).

Notice of Allowance and Fees Due (PTOL-85) for U.S. Appl. No. 18/153,624 Mailed on Sep. 6, 2024, 8 pages, United States Patent and Trademark Office, US.

* cited by examiner

SEGMENT-WISE PREDICTION MACHINE LEARNING FRAMEWORKS

CROSS-REFERENCES TO RELATED APPLICATION(S)

The present patent application claims priority to the U.S. Provisional Patent Application No. 63/266,682, filed on Jan. 12, 2022, which is incorporated by reference herein in its entirety.

BACKGROUND

The present disclosure addresses technical challenges related to the analysis of machine-learning-based digital data in an accurate, computationally efficient and predictively reliable manner. Existing systems are generally ill-suited to accurately, efficiently, and reliably analyze and/or generate data in various storage systems, such as storage systems that are associated with high-dimensional feature spaces with a high degree of size, diversity, and/or cardinality.

BRIEF SUMMARY

In general, embodiments of the present disclosure provide methods, apparatus, systems, computing devices, computing entities, and/or the like for analysis of digital data using artificial intelligence. Certain embodiments utilize methods, apparatus, systems, computing devices, computing entities, and/or the like for additionally performing actions based at least in part on the analysis of the digital data. Additionally, in certain embodiments, methods, apparatus, systems, computing devices, computing entities, and/or the like provide for a computer-based solution and/or a machine learning solution that provides for event valuation data forecasting.

In accordance with one embodiment, a computer-implemented method for generating a prediction output for a prediction input data object that is associated with a plurality of input segments is provided. The computer-implemented method provides for identifying a group of predictive codes, wherein each input segment is associated with a respective predictive code of the group of predictive codes. The computer-implemented method also provides for generating a document segment of an input document data object for the prediction input data object that is associated with the input segment, where the document segment is determined to be related to the respective predictive code for the input segment. The computer-implemented method also provides for generating, using a segment-wise prediction machine learning framework, and based at least in part on the document segment for the input segment and the respective predictive code for the input segment, a segment-wise prediction score for the input segment. In one or more embodiments, the segment-wise prediction machine learning framework comprises a text embedding machine learning model that is configured to generate a document embedding for the input segment based at least in part on the document segment for the input segment and a code embedding machine learning model that is configured to generate a code embedding for the respective predictive code for the input segment. In one or more embodiments, the segment-wise prediction machine learning framework is configured to generate the segment-wise prediction score for the input segment based at least in part on the document embedding for the input segment and the code embedding for the respective predictive code for the input segment. In one or more embodiments, the text embedding machine learning model is trained as part of a code prediction machine learning model that is configured to generate, for a particular input document data object, a selected code subset of the group of predictive codes. The computer-implemented method also provides for generating, based at least in part on each segment-wise prediction score, the prediction output. The computer-implemented method also provides for performing one or more prediction-based actions based at least in part on the prediction output.

In accordance with another embodiment, an apparatus comprising at least one processor and at least one memory including computer program code is provided. The at least one memory and the computer program code can be configured to, with the processor, cause the apparatus to identify a group of predictive codes, where each input segment is associated with a respective predictive code of the group of predictive codes. The at least one memory and the computer program code can also be configured to, with the processor, cause the apparatus to generate a document segment of an input document data object for the prediction input data object that is associated with the input segment, where the document segment is determined to be related to the respective predictive code for the input segment. The at least one memory and the computer program code can also be configured to, with the processor, cause the apparatus to generate, using a segment-wise prediction machine learning framework, and based at least in part on the document segment for the input segment and the respective predictive code for the input segment, a segment-wise prediction score for the input segment. In one or more embodiments, the segment-wise prediction machine learning framework comprises a text embedding machine learning model that is configured to generate a document embedding for the input segment based at least in part on the document segment for the input segment and a code embedding machine learning model that is configured to generate a code embedding for the respective predictive code for the input segment. In one or more embodiments, the segment-wise prediction machine learning framework is configured to generate the segment-wise prediction score for the input segment based at least in part on the document embedding for the input segment and the code embedding for the respective predictive code for the input segment. In one or more embodiments, the text embedding machine learning model is trained as part of a code prediction machine learning model that is configured to generate, for a particular input document data object, a selected code subset of the group of predictive codes. The at least one memory and the computer program code can also be configured to, with the processor, cause the apparatus to generate, based at least in part on each segment-wise prediction score, the prediction output. The at least one memory and the computer program code can also be configured to, with the processor, cause the apparatus to perform one or more prediction-based actions based at least in part on the prediction output.

In accordance with yet another embodiment, a computer program product is provided. The computer program product can comprise at least one non-transitory computer-readable storage medium comprising instructions, the instructions being configured to cause one or more processors to at least perform operations configured to identify a group of predictive codes, where each input segment is associated with a respective predictive code of the group of predictive codes. The instructions can also be configured to cause the one or more processors to at least perform operations configured to generate a document segment of an input document data object for the prediction input data object that is associated with the input segment, where the document segment is determined to be related to the respective predictive code for the input segment. The instructions can also be configured to cause the one or more processors to at least perform operations configured to generate, using a segment-wise prediction machine learning framework, and based at least in part on the document segment for the input segment and the respective predictive code for the input segment, a segment-wise prediction score for the input segment. In one or more embodiments, the segment-wise prediction machine learning framework comprises a text embedding machine learning model that is configured to generate a document embedding for the input segment based at least in part on the document segment for the input segment and a code embedding machine learning model that is configured to generate a code embedding for the respective predictive code for the input segment. In one or more embodiments, the segment-wise prediction machine learning framework is configured to generate the segment-wise prediction score for the input segment based at least in part on the document embedding for the input segment and the code embedding for the respective predictive code for the input segment. In one or more embodiments, the text embedding machine learning model is trained as part of a code prediction machine learning model that is configured to generate, for a particular input document data object, a selected code subset of the group of predictive codes. The instructions can also be configured to cause the one or more processors to at least perform operations configured to generate, based at least in part on each segment-wise prediction score, the prediction output. The instructions can also be configured to cause the one or more processors to at least perform operations configured to perform one or more prediction-based actions based at least in part on the prediction output.

BRIEF DESCRIPTION OF THE DRAWINGS

Having thus described the invention in general terms, reference will now be made to the accompanying drawings, which are not necessarily drawn to scale.

Figure 1:
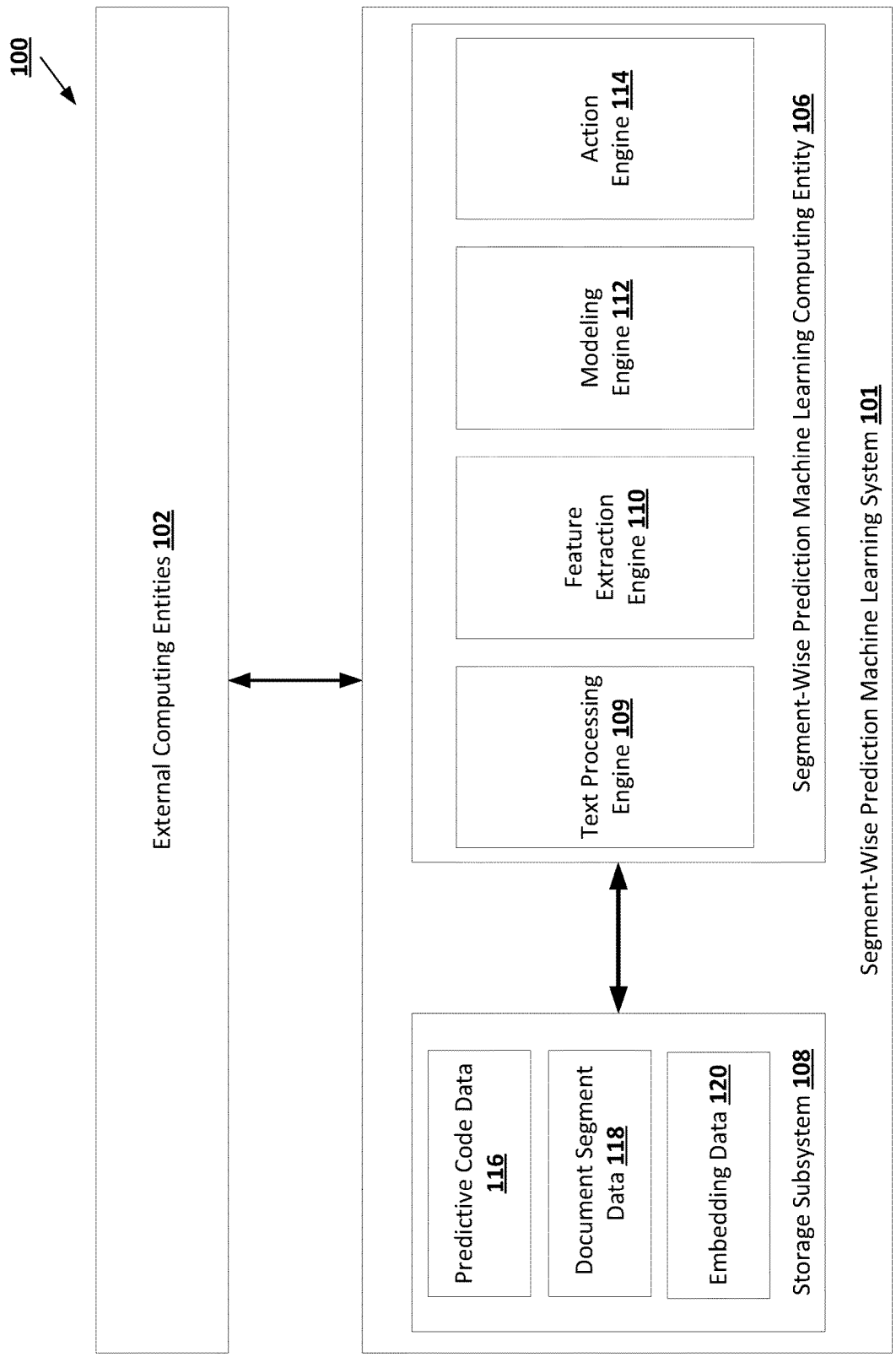

FIG. 1 provides an exemplary overview of an architecture that can be used to practice one or more embodiments of the present disclosure.

Figure 2:
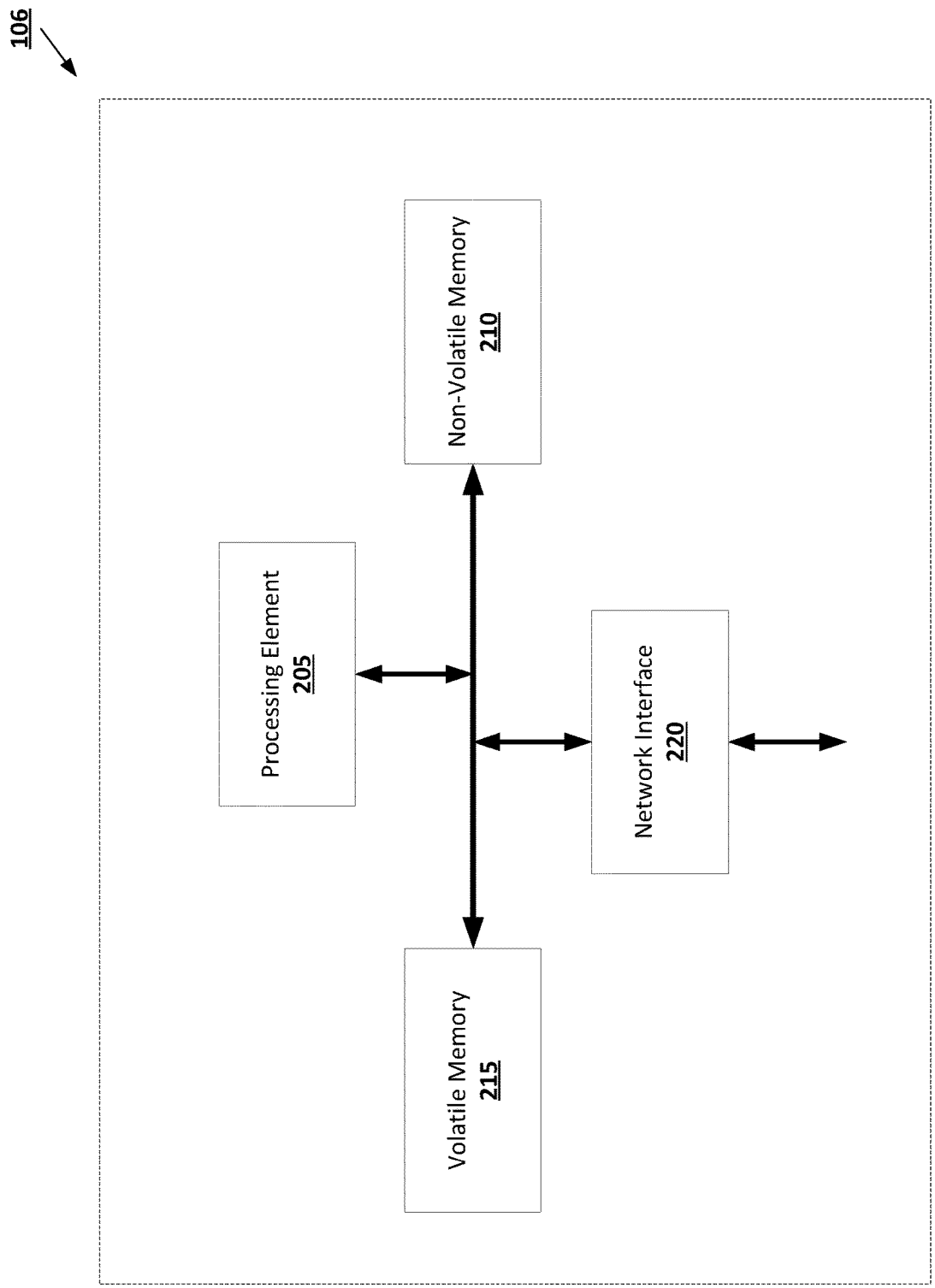

FIG. 2 provides an example segment-wise prediction machine learning computing entity in accordance with one or more embodiments discussed herein.

Figure 3:
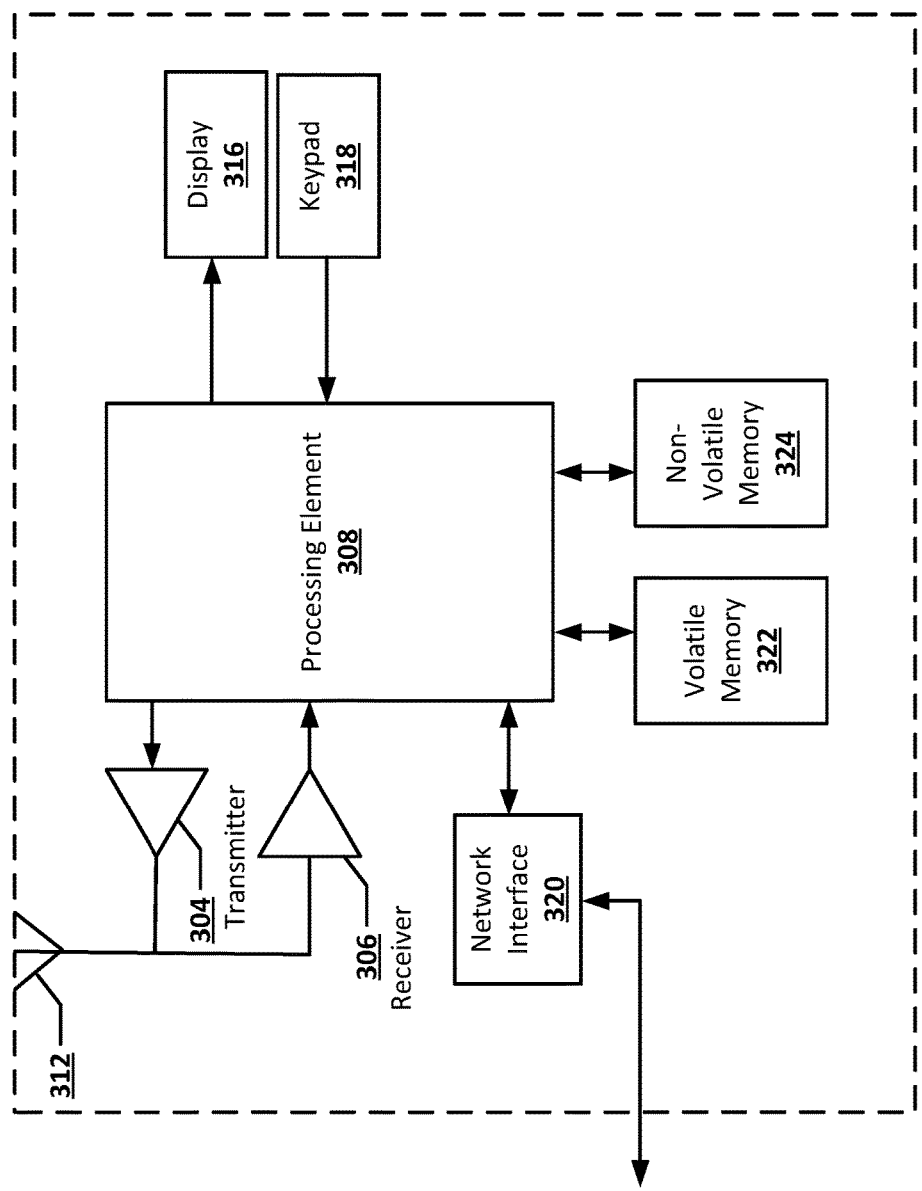

FIG. 3 provides an example external computing entity in accordance with one or more embodiments discussed herein.

Figure 4:
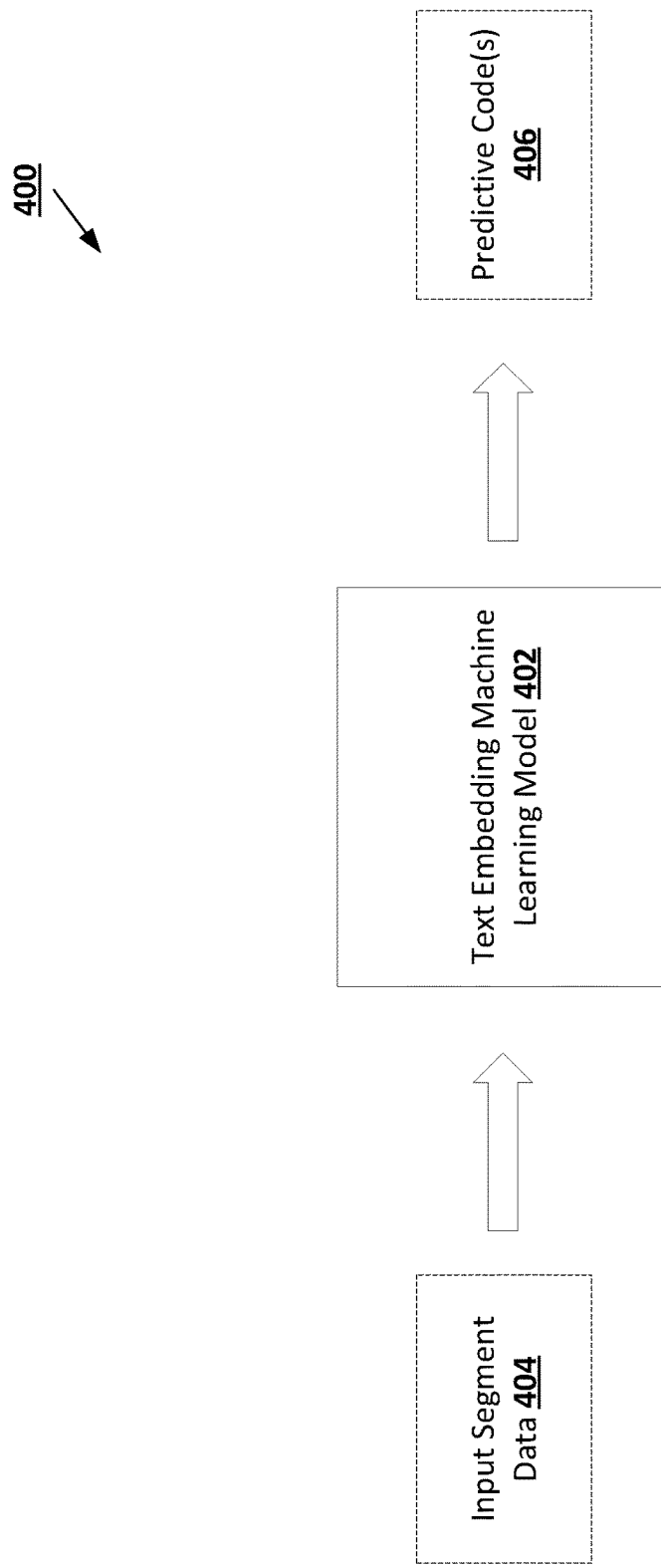

FIG. 4 provides an example system that provides for text embedding machine learning in accordance with one or more embodiments discussed herein.

Figure 5:
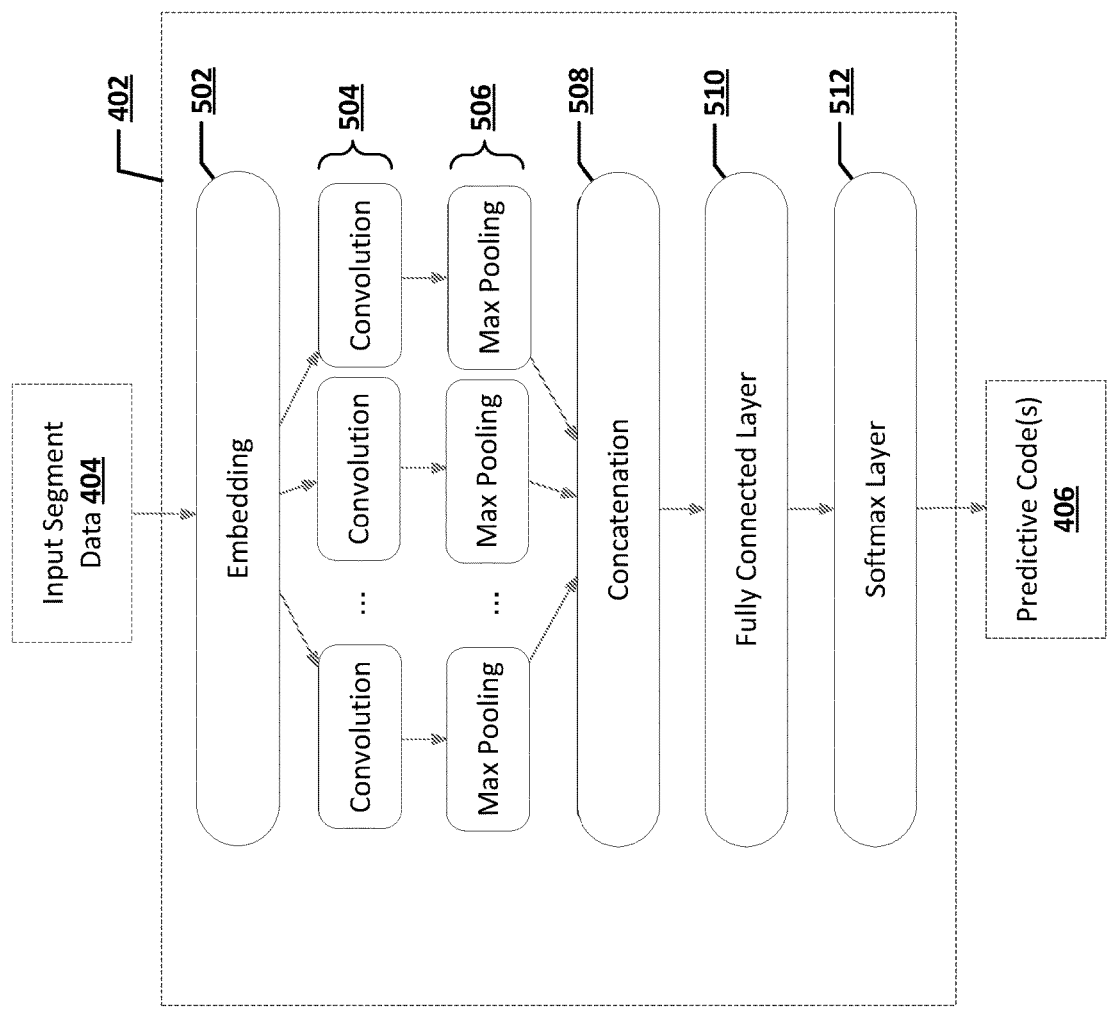

FIG. 5 provides another example system that provides for text embedding machine learning in accordance with one or more embodiments discussed herein.

Figure 6:
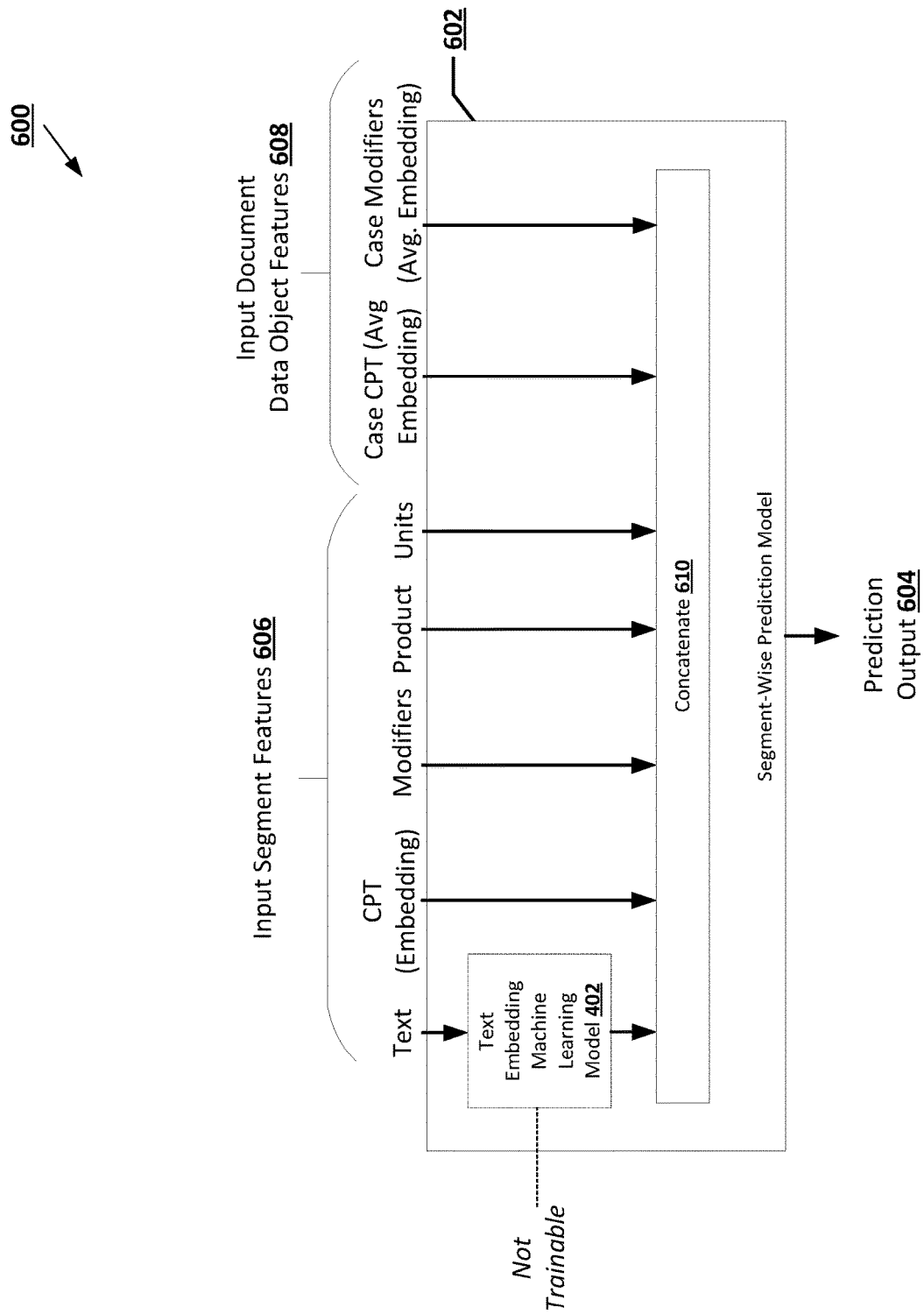

FIG. 6 provides an example segment-wise prediction machine learning framework in accordance with one or more embodiments discussed herein.

Figure 7:
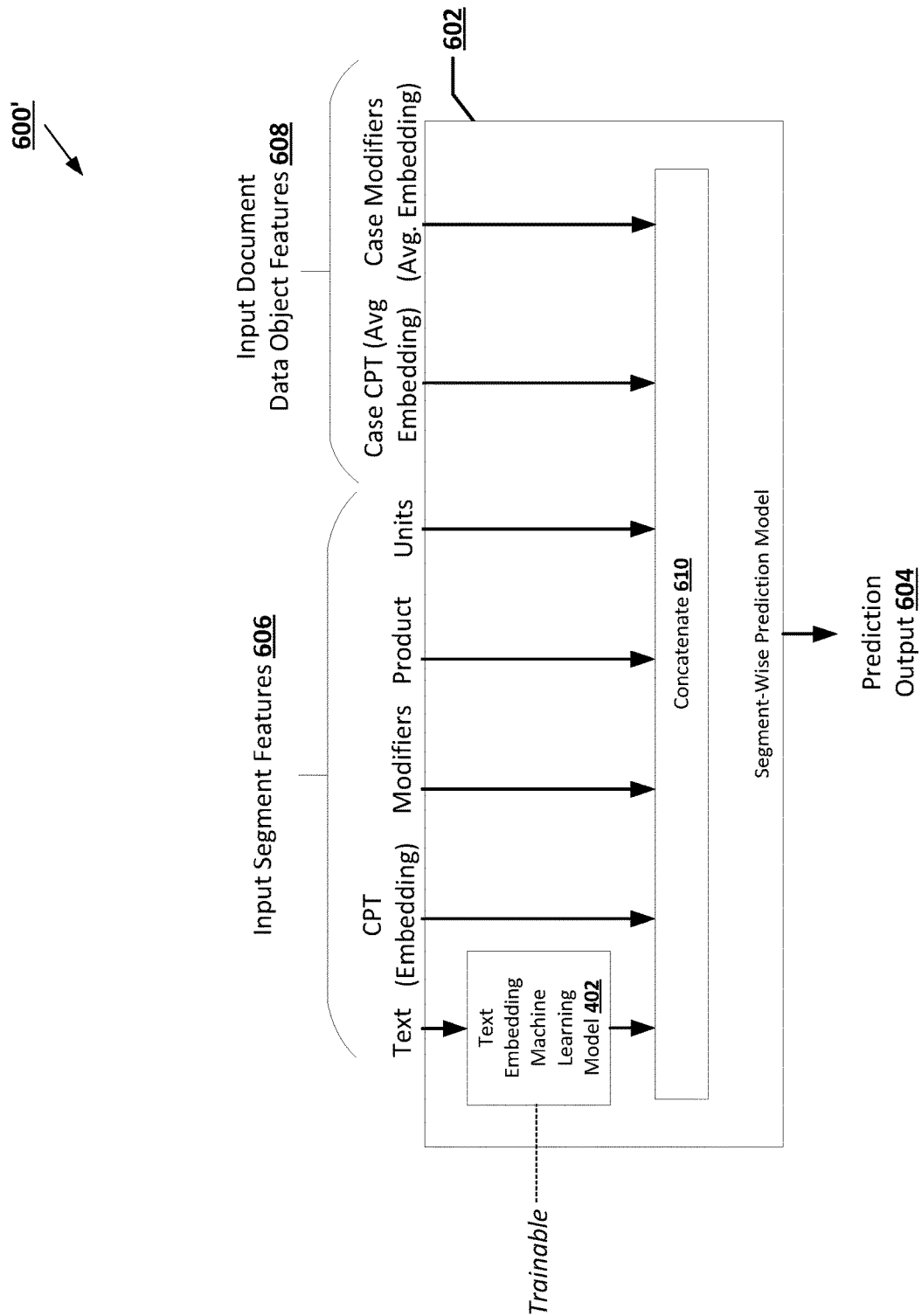

FIG. 7 provides another example segment-wise prediction machine learning framework in accordance with one or more embodiments discussed herein.

Figure 8:
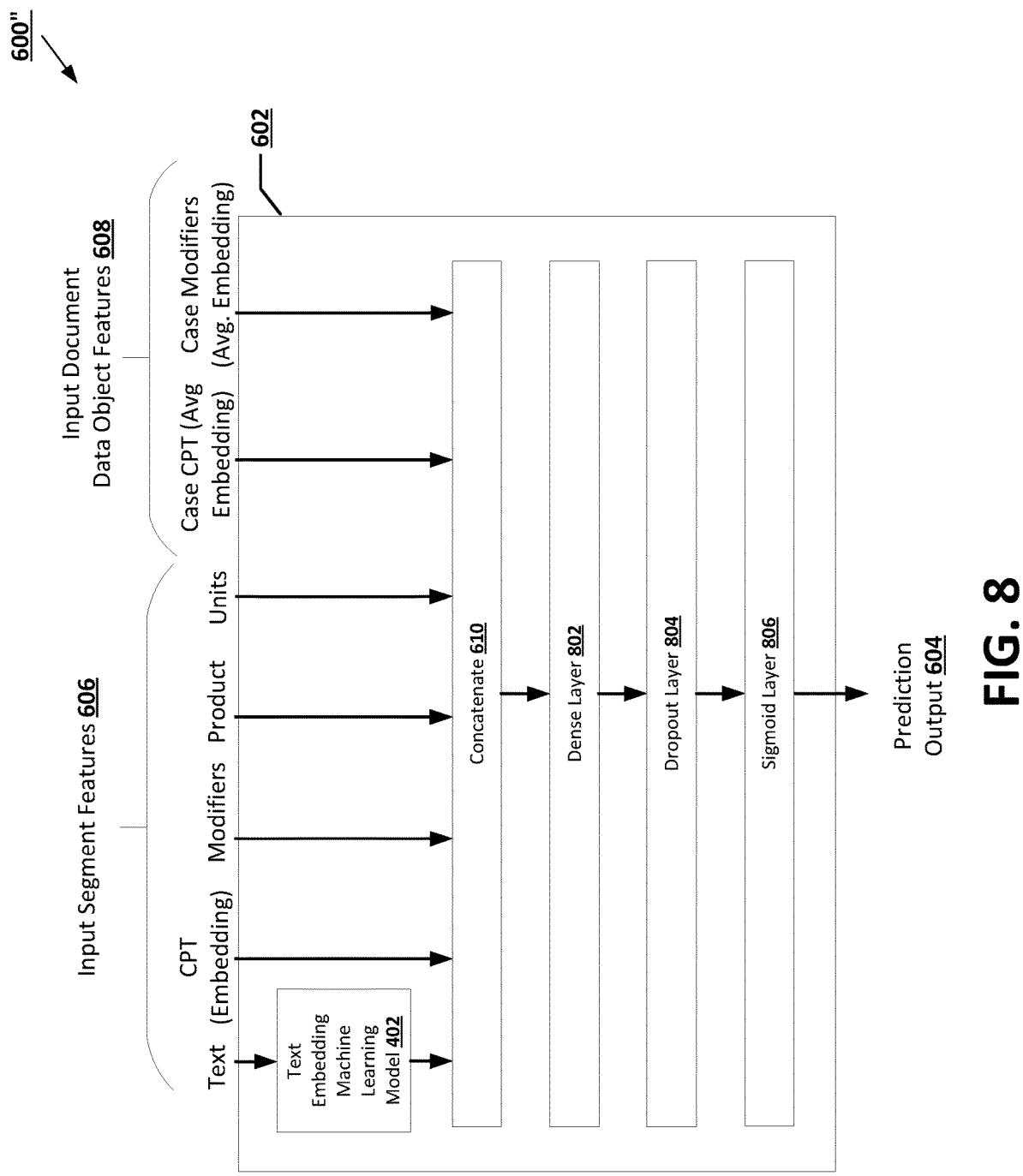

FIG. 8 provides yet another example segment-wise prediction machine learning framework in accordance with one or more embodiments discussed herein.

Figure 9:
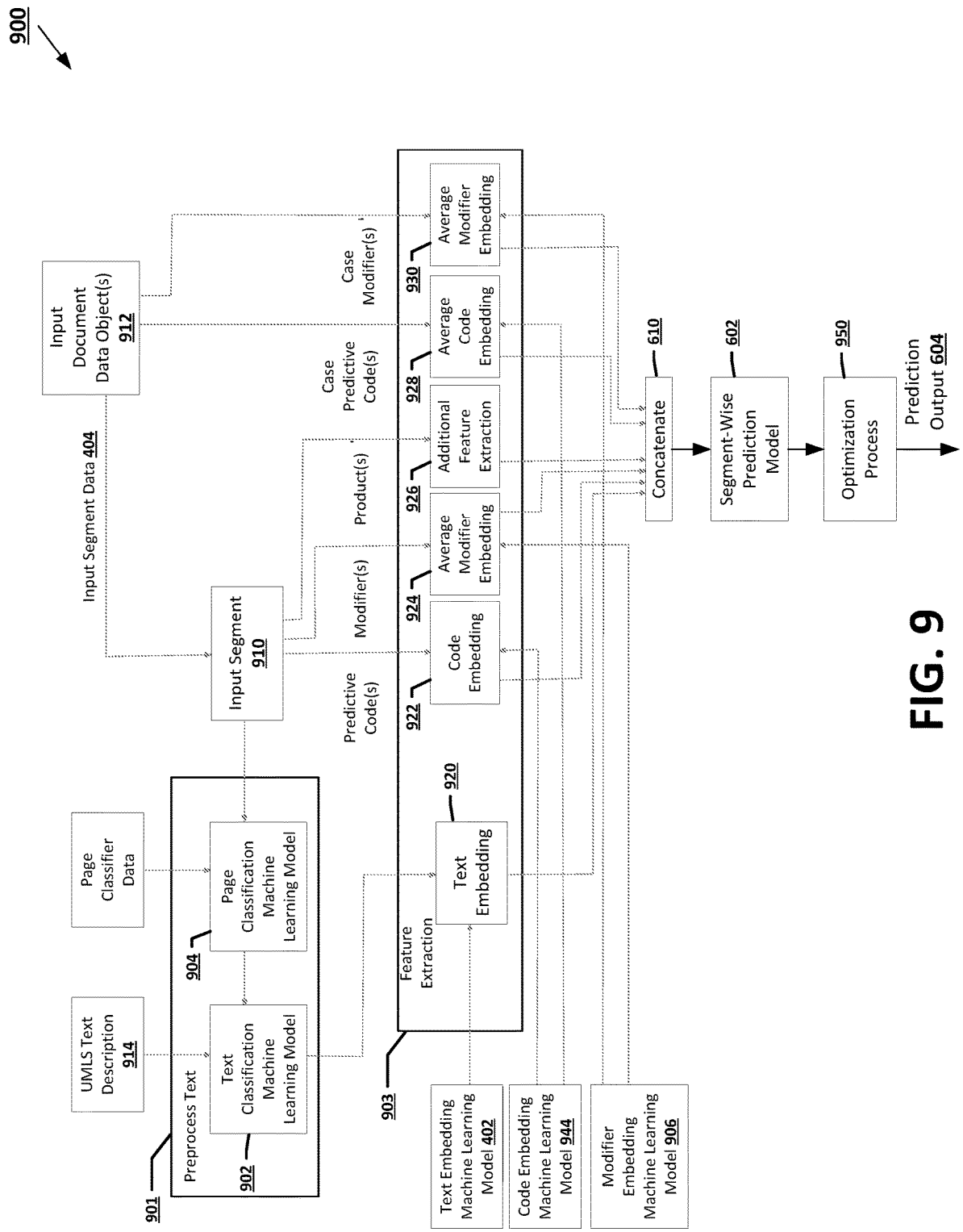

FIG. 9 provides an example machine learning system in accordance with one or more embodiments discussed herein.

Figure 10:
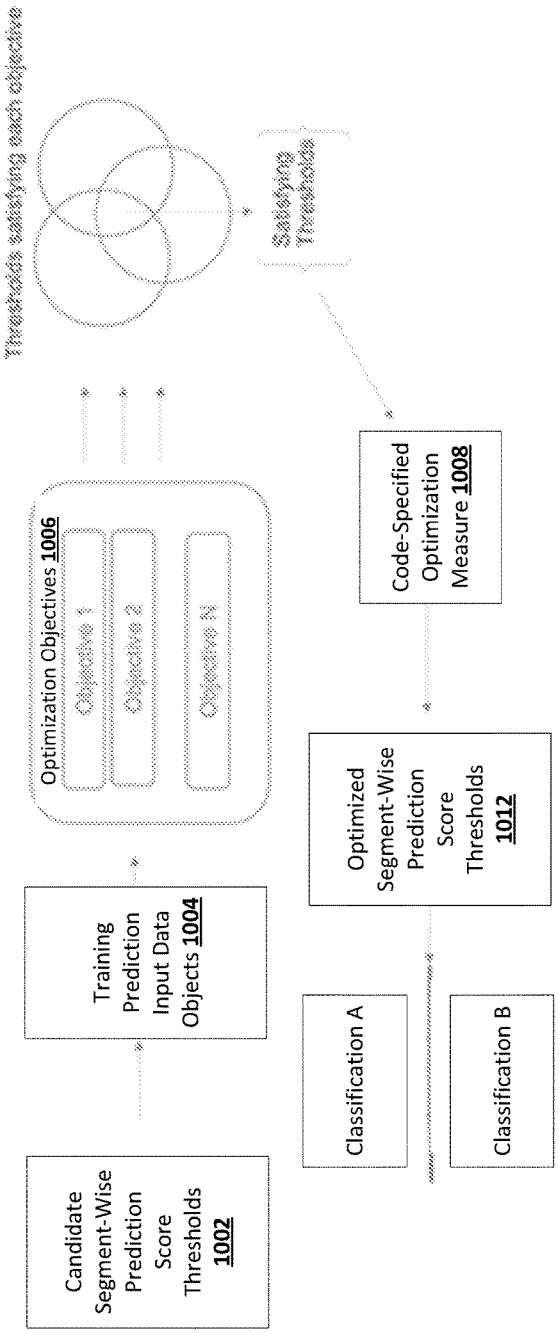

FIG. 10 provides an example optimization process in accordance with one or more embodiments discussed herein.

Figure 11:
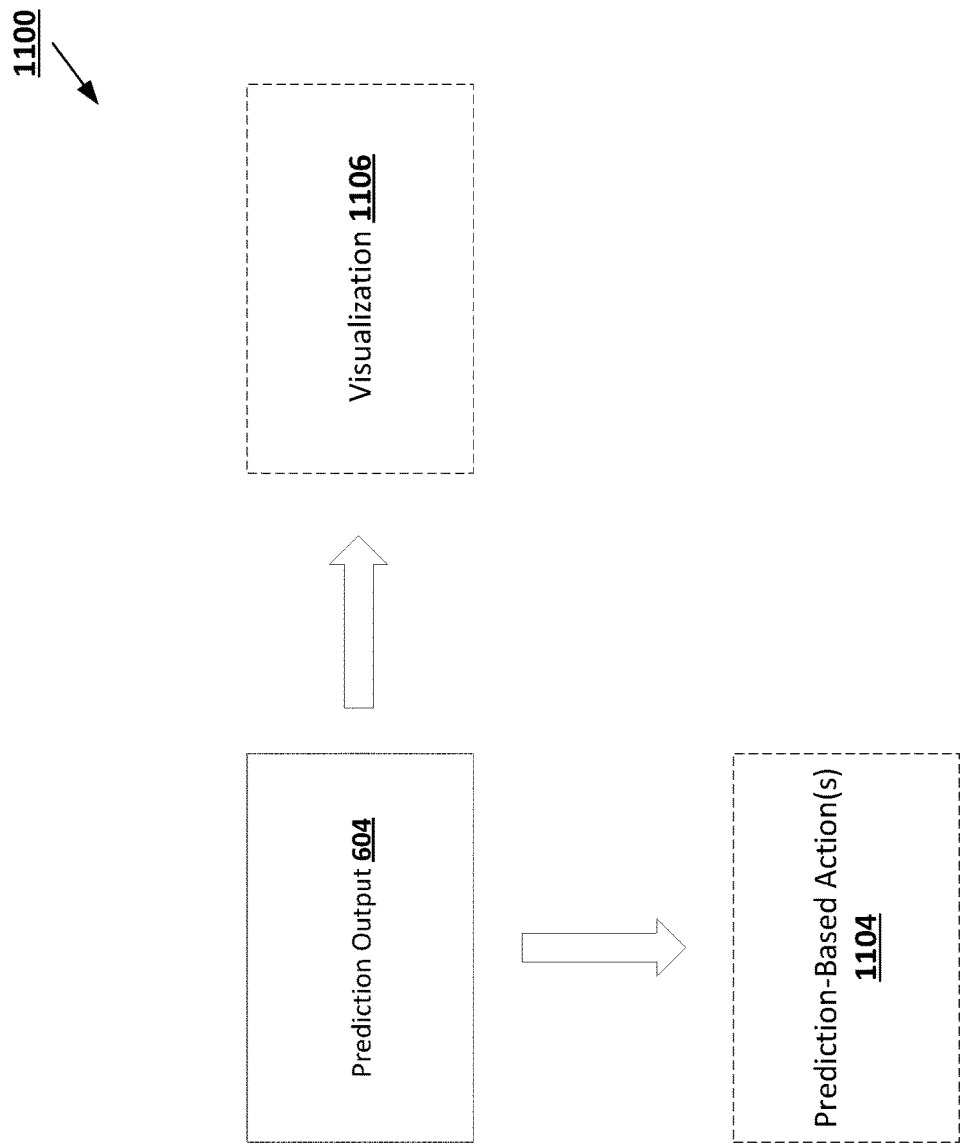

FIG. 11 provides an example system that provides for prediction-based actions and/or visualizations in accordance with one or more embodiments discussed herein.

Figure 12:
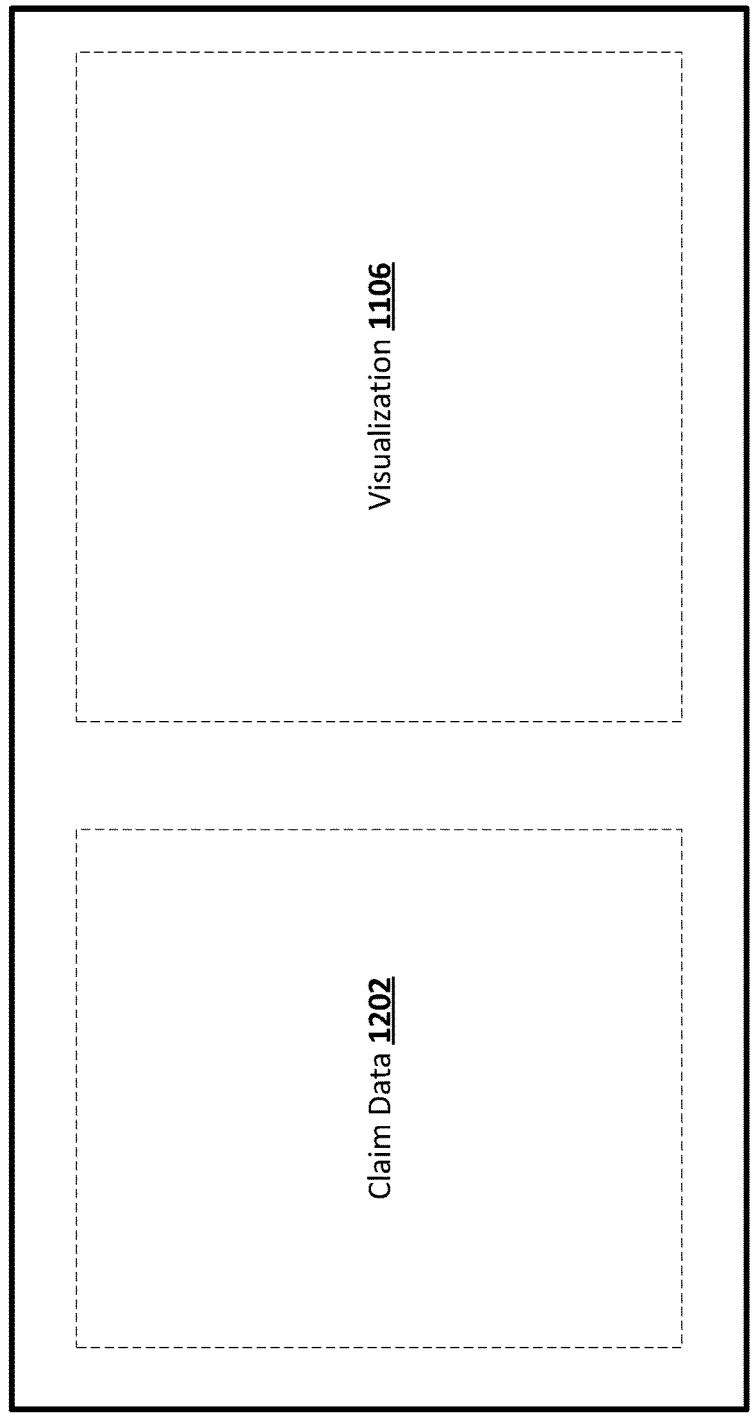

FIG. 12 provides an example user interface related to prediction-based visualizations in accordance with one or more embodiments discussed herein.

Figure 13:
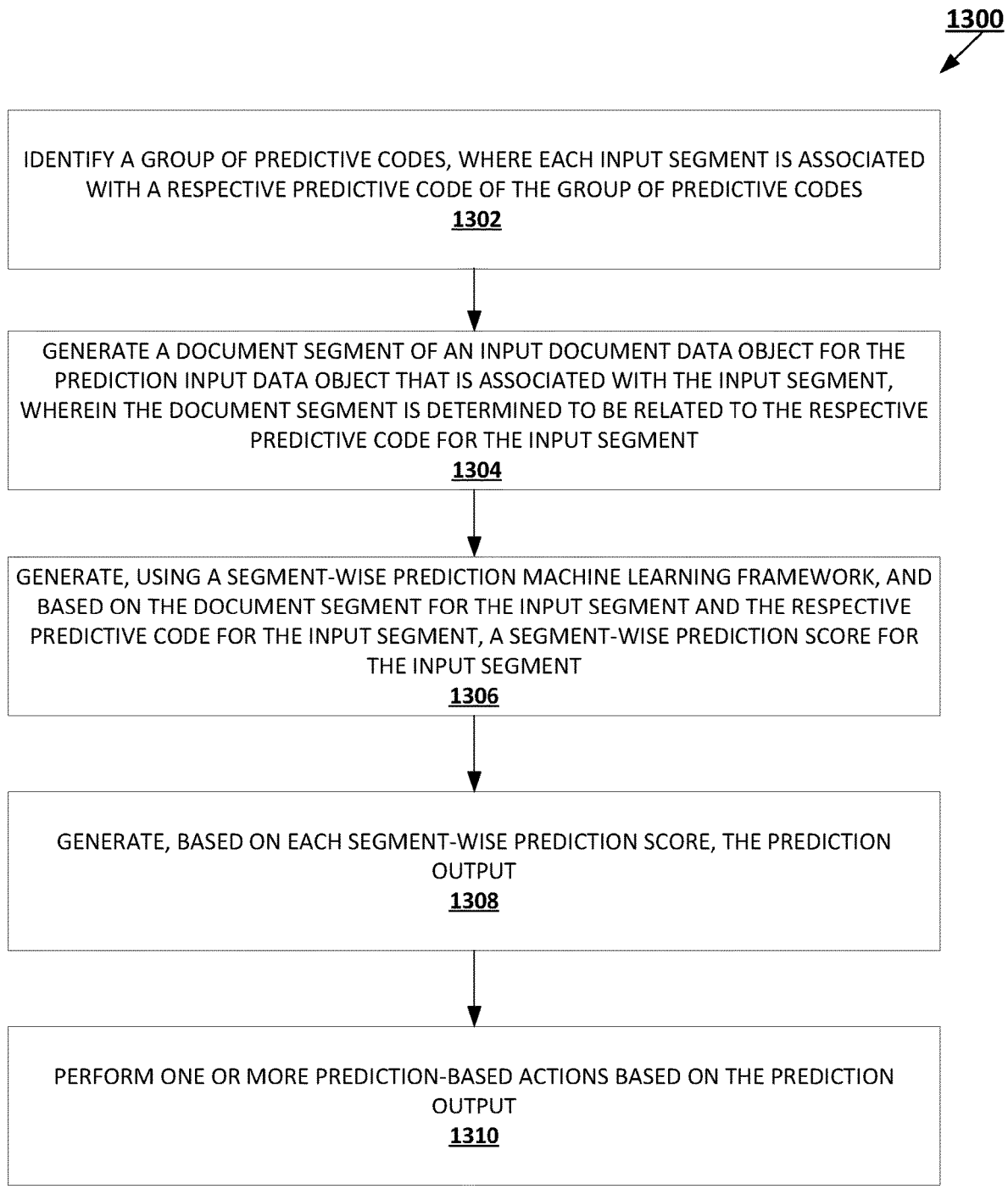

FIG. 13 is a flowchart diagram of an example process for generating a prediction output for a prediction input data object that is associated with a plurality of input segments in accordance with one or more embodiments discussed herein.

DETAILED DESCRIPTION

Various embodiments of the present disclosure now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present disclosure are described with reference to predictive data analysis, one of ordinary skill in the art will recognize that the disclosed concepts can be used to perform other types of data analysis.

I. OVERVIEW AND TECHNICAL IMPROVEMENTS

Various embodiments of the present invention introduce techniques that improve the training speed of segment-wise processing machine learning frameworks given a constant/target predictive accuracy by introducing a segment-wise processing machine learning framework architecture that comprises a text embedding machine learning model that is configured to generate a document embedding for the input segment based at least in part on the document segment for the input segment and a code embedding machine learning model that is configured to generate a code embedding for the respective predictive code for the input segment, where the segment-wise prediction machine learning framework is configured to generate the segment-wise prediction score for the input segment based at least in part on the document embedding for the input segment and the code embedding for the respective predictive code for the input segment, and the text embedding machine learning model is trained as part of a code prediction machine learning model that is configured to generate, for a particular input document data object, a selected code subset of the group of predictive codes. The combination of the noted components enables the proposed segment-wise processing machine learning framework to generate more accurate segment-wise predictions, which in turn increases the training speed of the proposed segment-wise processing machine learning framework given a constant predictive accuracy. It is well-understood in the relevant art that there is typically a tradeoff between predictive accuracy and training speed, such that it is trivial to improve training speed by reducing predictive accuracy, and thus the real challenge is to improve training speed without sacrificing predictive accuracy through innovative model architectures. See, e.g., Sun et al., *Feature-Frequency—Adaptive On-line Training for Fast and Accurate Natural Language*

*Processing* in 40(3) Computational Linguistic 563 at Abst. ("Typically, we need to make a tradeoff between speed and accuracy. It is trivial to improve the training speed via sacrificing accuracy or to improve the accuracy via sacrificing speed. Nevertheless, it is nontrivial to improve the training speed and the accuracy at the same time"). Accordingly, techniques that improve predictive accuracy without harming training speed, such as various techniques described herein, enable improving training speed given a constant predictive accuracy. Therefore, by improving accuracy of performing segment-wise machine learning predictions, various embodiments of the present invention improve the training speed of segment-wise processing machine learning frameworks given a constant/target predictive accuracy.

Moreover, various embodiments of the present invention make substantial technical improvements to performing operational load balancing for the post-prediction systems that perform post-prediction operations (e.g., automated specialist appointment scheduling operations) based at least in part on segment-wise predictive outputs. For example, in some embodiments, a predictive recommendation computing entity determines D classifications for D prediction input data objects based at least in part whether the selected region subset for each prediction input data object as generated by the predictive recommendation model comprises a target region (e.g., a target brain region). Then, the count of D prediction input data objects that are associated with an affirmative classification, along with a resource utilization ratio for each prediction input data object, can be used to predict a predicted number of computing entities needed to perform post-prediction processing operations with respect to the D prediction input data objects. For example, in some embodiments, the number of computing entities needed to perform post-prediction processing operations (e.g., automated specialist scheduling operations) with respect to D prediction input data objects can be determined based at least in part on the output of the equation: $R = \text{ceil}(\Sigma_k^{k=K} ur_k)$, where R is the predicted number of computing entities needed to perform post-prediction processing operations with respect to the D prediction input data objects, ceil(.) is a ceiling function that returns the closest integer that is greater than or equal to the value provided as the input parameter of the ceiling function, k is an index variable that iterates over K prediction input data objects among the D prediction input data objects that are associated with affirmative classifications, and $ur_k$ is the estimated resource utilization ratio for a kth prediction input data object that may be determined based at least in part on a patient history complexity of a patient associated with the prediction input data object. In some embodiments, once R is generated, a predictive recommendation computing entity can use R to perform operational load balancing for a server system that is configured to perform post-prediction processing operations with respect to D prediction input data objects. This may be done by allocating computing entities to the post-prediction processing operations if the number of currently-allocated computing entities is below R, and deallocating currently-allocated computing entities if the number of currently-allocated computing entities is above R.

Discussed herein are methods, apparatus, systems, computing devices, computing entities, and/or the like to facilitate event valuation forecasting using artificial intelligence. As will be recognized, the disclosed concepts can be used to perform any type of artificial intelligence for event valuation forecasting. Examples of artificial intelligence include, but are not limited to, machine learning, linear regression modeling, supervised machine learning, unsupervised machine learning, deep learning, neural network architectures, and/or the like.

Healthcare organizations often employ information from disparate database systems to facilitate providing one or more products and/or one or more services. However, it is generally difficult to accurately, efficiently, and/or reliably provide insights and forecasts related to data from disparate database systems. For example, the process of medical claim adjudication can be a lengthy and costly process that involves analysis of a vast amount of data from disparate database systems. As such, this medical record review process is often resource-intensive involving extensive time and/or a specialized skillset to review the medical records. Moreover, it is often difficult to achieve medical cost savings using traditional medical claim adjudication techniques.

During a typical medical claim adjudication process, a Payment Integrity (PI) analytic process can be employed to flag certain claims for which a corresponding medical record is to be submitted from the provider before the medical claim adjudication process can proceed. However, before a medical record can be sent off for clinical review, a medical record is generally analyzed via a series of non-clinical checks in which medical record legibility, patient information, date-of-service information, and/or potential payment information are examined. Once a medical record is analyzed, the medical record is generally sent for clinical review where a team of specialized coders reviews the medical record and the corresponding claim to ensure that all claim lines and Current Procedural Terminology (CPT) codes are supported in the medical record. A reviewer can then provide a recommendation decision to pay or deny the claim.

Certain traditional medical claim adjudication techniques can employ a combination of optical character recognition (OCR) technology and/or keyword logic. For example, medical record review techniques can obtain medical record images and can convert the medical record images into text via OCR. Keyword logic can then be applied on a subset of CPT codes to search for known keywords and/or to apply related logic to provide a "pay" or "deny" decision. However, a claim often contains multiple claim lines, and obtaining a "pay" decision on a singular claim line is not efficient. In fact, a reviewer is still required to open the medical record and assess the remaining claim lines in order to "close out" the case. As such, the aforementioned medical record review techniques generally require further scaling to cover a broader range of CPT codes and/or to provide logic to ignore certain claim lines if it would be more efficient to close out the case based at least in part on a single-line payment decision. Given that there are generally over 10,000 possible CPT codes for a medical recorder, these traditional medical claim adjudication techniques are generally extremely labor-intensive and often introduce numerous critical errors during the medical record review process.

Other traditional medical claim adjudication techniques employ a machine learning model to learn the function for mapping claims data and medical records to a PI review decision using historical case information as training data. For example, a machine learning model can be provided based at least in part on a Unified Medical Language System (UMLS) ontology and a corresponding hierarchical structure for CPT codes in which groups of similar CPT codes are grouped together under shared parent nodes.

According to some embodiments, machine learning models can be trained using subsets of data relevant to a respective level in the ontological hierarchy, and each output of a machine learning model can produce a single prediction value. Accordingly, identification of high-level patterns for certain related groups can be provided. However, such a solution often involves a high-level of complexity for monitoring and/or maintenance of the machine learning models. For example, hundreds of unique models are generally required to achieve a single claim line prediction. Additionally, medical records often contain multiple claim lines along with information for all claim lines in a case, and the relevant information may be a singular paragraph or set of keywords in the entire record. OCR errors are also common with traditional machine learning modeling. Moreover, human reviewers often disagree on review results and there are often thousands of possible unique CPT codes that can occur with varying frequency, resulting in possible inaccurate claim pay/deny classifications. As such, existing technological solutions for providing insights and/or forecasts related to data from disparate database systems remains a challenge.

Various embodiments of the present disclosure address technical challenges related to providing insights and/or forecasts related to data from disparate database systems. In various embodiments, a segment-wise prediction machine learning framework is provided. The segment-wise prediction machine learning framework can be configured to provide insights, forecasts, and/or predictions related to data from disparate database systems. In various embodiments, the segment-wise prediction machine learning framework provides generalizability and/or specificity within a machine learning model for improved medical record classifications. In various implementations, the segment-wise prediction machine learning framework employs a machine learning model configured for clinical decision automation together with a clinical review process. The segment-wise prediction machine learning framework can additionally or alternatively employ deep learning model using transfer learning and/or CPT thresholds. For example, deep learning model can learn rules for automated clinical review of medical records and/or claims.

In various embodiments, the segment-wise prediction machine learning framework can include a text embedding machine learning model. The text embedding machine learning model can be trained to predict a set of CPT codes. For example, the text embedding machine learning model can be trained for learning of features unique to the CPT codes. In certain embodiments, the text embedding machine learning model can be a CPT model. The segment-wise prediction machine learning framework can additionally or alternatively include a segment-wise classification machine learning model. In various embodiments, a pre-trained version of the text embedding machine learning model can be applied to the segment-wise classification machine learning model using transfer learning. In certain embodiments, the segment-wise classification machine learning model can be a pay/deny prediction model. Additionally, in various embodiments, the segment-wise classification machine learning model can be tuned using a trained version of the text embedding machine learning model. Accordingly, improved learning of differences between a payment/denial classification can be provided. The segment-wise prediction machine learning framework can also be robust to small variations in language associated with data such as, for example, medical records.

In various embodiments, optimized CPT specific thresholds can be employed for decision boundaries to optimize prediction boundaries for objectives across CPT codes. Additionally, features provided to the segment-wise classification machine learning model can include, for example, CPT embeddings to provide for learning of similarities between CPT codes. The features can additionally or alternatively include case-level CPT and modifier embeddings to provide for learning of claim line inter-dependencies (e.g., such as CPT codes that should not be billed together). In certain embodiments, to facilitate modeling by the segment-wise prediction machine learning framework, a pre-processing pipeline can be employed to, for example, remove identified irrelevant content and/or employ a page-level UMLS similarity calculation to uniquely filter medical records for respective claim lines. Accordingly, an amount of medical record text that is processed by the segment-wise prediction machine learning framework can be reduced (e.g., to reduce the amount of computing resources employed by the modeling by only providing models with relevant portions of the medical record text). In certain embodiments, a front-end visualization can also be provided for end-users to engage with the forecasted output, insights, predictions, and/or classifications.

The segment-wise prediction machine learning framework provides significant advantages over existing technological solutions such as, for example, improved integrability, reduced complexity, improved accuracy, and/or improved speed as compared to existing technological solutions. Accordingly, by employing various techniques related to the segment-wise prediction machine learning framework disclosed herein, various embodiments of the present disclosure enable utilizing efficient and reliable machine learning solutions to process high-dimensional feature spaces with a high degree of size, diversity and/or cardinality. In doing so, various embodiments of the present disclosure address shortcomings of existing system solutions and enable solutions that are capable of accurately, efficiently and/or reliably providing forecasts, insights, and classifications to facilitate optimal decisions and/or actions related to the health information. Moreover, by employing various techniques related to the segment-wise prediction machine learning framework disclosed herein, one or more other technical benefits can be provided, including improved interoperability, improved reasoning, reduced errors, improved information/data mining, improved analytics, and/or or the like related to machine learning. Accordingly, the segment-wise prediction machine learning framework disclosed herein provides improved predictive accuracy without reducing training speed and also enable improving training speed given a constant predictive accuracy. In doing so, the techniques described herein improve efficiency and speed of training machine learning models, thus reducing the number of computational operations needed and/or the amount of training data entries needed to train machine learning models. Accordingly, the techniques described herein improve at least one of the computational efficiency, storage-wise efficiency, and speed of training machine learning models.

II. DEFINITIONS OF CERTAIN TERMS

The term "prediction output" may refer to a data construct that describes one or more prediction insights, classifications, and/or inferences provided by one or more machine learning models. In various embodiments, prediction insights, classifications, and/or inferences may be with respect to one or more data objects and/or features of one or more groupings of text such as, for example, one or more portions of a document. In certain embodiments, a prediction output can provide a prediction as to whether a claim line of a medical record should be paid or denied. For example, in certain embodiments, a prediction output can provide a "pay" or "deny" decision for one or more claim lines of a medical record.

The term "input document data object" may refer to a data construct that describes a collection of text data. For example, in certain embodiments, an input document data object may correspond to a medical record. A medical record (e.g., typically multiple pages) may contain information for all claim lines in a case. A portion of a medical record for a particular claim line may be one paragraph or a set of keywords in the medical record.

The term "prediction input data object" may refer to a data construct that describes a real world entity and/or a virtual entity with respect to which one or more predictive data analysis operations are performed. An example of a prediction input data object is a medical/health insurance claim. In various embodiments, a prediction input data object may be associated with a set of C predictive codes and/or an input document data object having a set of C document segments. In various embodiments, each document segment may be associated with a respective one of the C predictive codes, such that there is a one-to-one relationship between the set of predictive codes and the set of document segments. In certain embodiments, a prediction input data object may refer to a claim of a medical record.

The term "input segment" may refer to a data construct that describes one or more portions of the prediction input data object. In certain embodiments, an input segment may refer to a claim line of a medical record.

The term "predictive code" may refer to a data construct that describes an identifier for one or more tasks, one or more services, and/or one or more actions related to the input segment. In certain embodiments, a predictive code may be a medical code employed to report one or more tasks, one or more services, and/or one or more actions related to a medical record. For example, in certain embodiments, a predictive code may be a current procedural terminology (CPT) code. In certain embodiments, a predictive code may be selected from a set of predictive codes stored in a data structure.

The term "document segment" may refer to a data construct that describes a segment of an input document data object that is deemed related to a predictive code. For example, in certain embodiments, a document segment may correspond to a segment of a medical record that is deemed related to a CPT code for a claim line.

The term "segment-wise prediction machine learning framework" may refer to a data construct that describes parameters, hyperparameters, and/or defined operations of one or more machine learning models configured to generate a predictive output for a prediction input data object. In some embodiments, the segment-wise prediction machine learning framework process one or more input segments, one or more document segments, one or more predictive codes, and/or other data related to one or more input document data objects. A segment-wise prediction machine learning framework may be configured to provide a segment-wise prediction score for one or more input segments, one or more document segments, one or more predictive codes, and/or other data related to one or more input document data objects via respective attributes and/or features applied to the one or more machine learning techniques in a segment-wise grouping of the respective attributes and/or features.

A "segment-wise prediction score" may refer to a data construct that describes a particular prediction described by a predictive output for a respective input segment of the prediction input data object. In some embodiments, the segment-wise prediction score for an input segment is a score that corresponds to a probability for a particular insight, classification, and/or inference provided by the segment-wise prediction machine learning framework. For example, in certain embodiments, a segment-wise prediction score may correspond to a pay/deny probability for a claim line.

A "text embedding machine learning model" may refer to a data construct that describes parameters, hyperparameters, and/or defined operations of a machine learning model that is configured to generate a document embedding for an input segment using one or text embedding machine learning techniques. In various embodiments, a text embedding machine learning model may employ natural language processing to generate an inferred predictive code for respective input segments. In certain embodiments, a text embedding machine learning model is trained based at least in part on ground-truth natural language outputs (e.g., ground-truth text classifications, ground-truth text translations/summarizations, and/or the like) for a set of training input text embeddings, such as ground-truth natural language outputs determined based at least in part on subject matter annotations and/or ground-truth natural language outputs for particular text documents. In certain embodiments, a text embedding machine learning model may be configured as a neural network model and/or a deep learning model. In certain embodiments, a text embedding machine learning model may be configured as a CPT model.

A "code embedding machine learning model" may refer to a data construct that describes parameters, hyperparameters, and/or defined operations of a machine learning model that is configured to generate one or more code embeddings related to respective predictive codes. A code embedding may be embedding a data representation (e.g., a data vector representation) configured to be utilized by the segment-wise prediction machine learning framework. In various embodiments, a code embedding machine learning model may employ natural language processing to generate an inferred code embedding for respective predictive codes. In certain embodiments, a code embedding machine learning model is trained based at least in part on ground-truth outputs (e.g., ground-truth code classifications and/or the like) for a set of training input code embeddings. In certain embodiments, a code embedding machine learning model may be configured as a neural network model and/or a deep learning model. In certain embodiments, a code embedding machine learning model may be configured as a CPT embedding model.

A "code prediction machine learning model" may refer to a data construct that describes parameters, hyperparameters, and/or defined operations of a machine learning model that is configured to generate a selected code subset of the group of predictive codes for a particular input document data object. In various embodiments, a code prediction machine learning model may be configured to provide a prediction output and/or one or more segment-wise prediction score. In various embodiments, the text embedding machine learning model may be integrated into the code prediction machine learning model. In various embodiments, the text embedding machine learning model may be trained as part of the code prediction machine learning model. In certain embodiments, a code prediction machine learning model is trained based at least in part on ground-truth prediction outputs (e.g., ground-truth prediction classifications and/or the like) for a set of training input segment features and/or a set of training input data object features. In certain embodiments, a code embedding machine learning model may be configured as a neural network model and/or a deep learning model. In certain embodiments, a code prediction machine learning model may be configured as a pay/deny prediction model.

A "page classification machine learning model" may refer to a data construct that describes parameters, hyperparameters, and/or defined operations of a machine learning model that is configured to remove one or more portions (e.g., one or more pages) of a document based at least in part on respective page classifications for the pages of the document. In various embodiments, a page classification machine learning model may employ natural language processing to generate an inferred page classification. In certain embodiments, a page classification machine learning model is trained based at least in part on ground-truth natural language outputs (e.g., ground-truth page classifications, ground-truth page translations/summarizations, and/or the like) for a set of training input pages for particular text documents. In certain embodiments, a page classification machine learning model may be configured as a neural network model and/or a deep learning model.

III. COMPUTER PROGRAM PRODUCTS, METHODS, AND COMPUTING ENTITIES

Embodiments of the present disclosure may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of an apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations. Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM ARCHITECTURE

FIG. 1 provides an exemplary overview of an architecture 100 that can be used to practice embodiments of the present disclosure. The architecture 100 includes a segment-wise prediction machine learning system 101 and one or more external computing entities 102. For example, at least some of the one or more external computing entities 102 can provide inputs to the segment-wise prediction machine learning system 101. Additionally or alternatively, at least some of the one or more external computing entities 102 can receive decision outputs, task outputs and/or action outputs from the segment-wise prediction machine learning system 101 in response to providing the inputs. As another example, at least some of the external computing entities 102 can provide one or more data streams and/or one or more batch loads to the segment-wise prediction machine learning system 101 and request performance of particular prediction-based actions in accordance with the provided one or more data streams and/or one or more batch loads. As a further example, at least some of the external computing entities 102 can provide training data to the segment-wise prediction machine learning system 101 and request training of one or more machine learning models in accordance with the provided training data. In some of the noted embodiments, the segment-wise prediction machine learning system 101 can be configured to transmit parameters, hyper-parameters, and/or weights of a trained machine learning model to the external computing entities 102.

In some embodiments, the segment-wise prediction machine learning system 101 can include a segment-wise prediction machine learning computing entity 106. The segment-wise prediction machine learning computing entity 106 and the external computing entities 102 can be configured to communicate over a communication network (not shown). The communication network can include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

Additionally, in some embodiments, the segment-wise prediction machine learning system 101 can include a storage subsystem 108. The segment-wise prediction machine learning computing entity 106 can be configured to provide one or more predictions using one or more artificial intelligence techniques and/or one or more machine learning techniques. For instance, the segment-wise prediction machine learning computing entity 106 can be configured to determine forecasts, insights, predictions, and/or classifications related to data from disparate database systems. The segment-wise prediction machine learning computing entity 106 can be additionally or alternatively configured to compute optimal decisions, display optimal data for a dashboard (e.g., a graphical user interface), generate optimal data for reports, optimize actions, and/or optimize configurations associated with a decision management system, a workflow management system, a clinical decision automation system, a medical claim adjudication system, a clinical review system, and/or another type of system. The segment-wise prediction machine learning computing entity 106 includes a text processing engine 109, a feature extraction engine 110, a modeling engine 112, and/or an action engine 114. In some embodiments, the text processing engine 109 can perform pre-processing with respect to text to remove non-relevant text and/or irrelevant pages of one or more document segments. In some embodiments, the feature extraction engine 110 can perform feature extractions associated with one or more document segments to determine a set of embeddings (e.g., a set of document embeddings and/or a set of code embeddings). In some embodiments, the modeling engine 112 can determine one or more predictions and/or classifications based at least in part on predictive code data 116, document segment data 118, and/or embedding data 120. The predictive code data 116 can include a group of predictive codes. The document segment data 118 can include data for one or more document segments of one or more input document data objects. An input document data object can be, for example, a medical record for a claim. A document segment can be, for example, a segment of a medical record that is deemed to be related to a predictive code for a claim line. The embedding data 120 can include the set of embeddings determined by the feature extraction engine 110. The action engine 114 can employ the one or more predictions and/or classifications associated with the modeling engine 112 to perform one or more actions. In certain embodiments, the action engine 114 can employ the one or more predictions and/or classifications associated with the modeling engine 112 to provide one or more visualizations via user interface of a display (e.g., display 316). In certain embodiments, the action engine 114 can employ the one or more predictions and/or classifications associated with the modeling engine 112 to optimize one or more machine learning models employed by the modeling engine 112. As such, the segment-wise prediction machine learning computing entity 106 can provide accurate, efficient and/or reliable predictions and/or classifications using machine learning. Further example operations of the modeling engine 112, and/or the action engine 114 are described with reference to FIGS. 4-9.

In one or more embodiments, the predictive code data 116, the document segment data 118, and/or the embedding data 120 can be stored in the storage subsystem 108. The storage subsystem 108 can include one or more storage units, such as multiple distributed storage units that are connected through a computer network. In certain embodiments, the predictive code data 116, the document segment data 118, and/or the embedding data 120 can be stored in disparate storage units (e.g., disparate databases) of the storage subsystem 108. Each storage unit in the storage subsystem 108 can store at least one of one or more data assets and/or one or more data about the computed properties of one or more data assets. Moreover, each storage unit in the storage subsystem 108 can include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Various embodiments provide technical solutions to technical problems corresponding to data processing. In particular, data processing techniques related to data stored in disparate data sources tends to be resource intensive and time intensive. For example, continually querying a data structure would significantly slow down a data ingestion processes and/or would require significantly more computational resources. However, with the architecture 100 and one or more other embodiments disclosed herein, one or more technical improvements can be provided such as a reduction in computationally intensiveness and time intensiveness needed for automated managing, ingesting, monitoring, updating, and/or extracting/retrieving of data for providing segment-wise prediction using machine learning. With the architecture 100 and one or more other embodiments disclosed herein, reduction in computational resources required for automated managing, ingesting, monitoring, updating, and/or extracting/retrieving of data for providing segment-wise prediction using machine learning can also be provided. The architecture 100 can also allocate processing resources, memory resources, and/or other computational resources to other tasks while executing one or more processes related to providing segment-wise prediction using machine learning in parallel. As such, various embodiments of the present disclosure therefore provide improvements to the technical field of processing and/or analyzing data from disparate network systems. In certain embodiments, a graphical user interface of a computing device that renders at least a portion of segment-wise predictions, classifications, and/or insights can also be improved.

Exemplary Artificial Intelligence Computing Entity

FIG. 2 provides a schematic of the segment-wise prediction machine learning computing entity 106 according to one embodiment of the present disclosure. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes can include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the segment-wise prediction machine learning computing entity 106 can also include a network interface 220 for communicating with various computing entities, such as by communicating data, content, information, and/or similar terms used herein interchangeably that can be transmitted, received, operated on, processed, displayed, stored, and/or the like. Furthermore, it is to be appreciated that the network interface 220 can include one or more network interfaces.

As shown in FIG. 2, in one embodiment, the segment-wise prediction machine learning computing entity 106 can include or be in communication with processing element 205 (also referred to as processors, processing circuitry, and/or similar terms used herein interchangeably) that communicate with other elements within the segment-wise prediction machine learning computing entity 106 via a bus, for example. It is to be appreciated that the processing element 205 can include one or more processing elements. As will be understood, the processing element 205 can be embodied in a number of different ways. For example, the processing element 205 can be embodied as one or more complex programmable logic devices (CPLDs), microprocessors, multi-core processors, coprocessing entities, application-specific instruction-set processors (ASIPs), microcontrollers, and/or controllers. Further, the processing element 205 can be embodied as one or more other processing devices or circuitry. The term circuitry can refer to an entirely hardware embodiment or a combination of hardware and computer program products. Thus, the processing element 205 can be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 can be configured for a particular use or configured to execute instructions stored in volatile or non-volatile media or otherwise accessible to the processing element 205. As such, whether configured by hardware or computer program products, or by a combination thereof, the processing element 205 can be capable of performing steps or operations according to embodiments of the present disclosure when configured accordingly.

In one embodiment, the segment-wise prediction machine learning computing entity 106 can further include or be in communication with non-volatile memory 210. The non-volatile memory 210 can be non-volatile media (also referred to as non-volatile storage, memory, memory storage, memory circuitry, and/or similar terms used herein interchangeably). Furthermore, in an embodiment, non-volatile memory 210 can include one or more non-volatile storage or memory media, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media can store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably can refer to a collection of records or data that is stored in a computer-readable storage medium using one or more database models, such as a hierarchical database model, network model, relational model, entity-relationship model, object model, document model, semantic model, graph model, and/or the like.

In one embodiment, the segment-wise prediction machine learning computing entity 106 can further include or be in communication with volatile memory 215. The volatile memory 215 can be volatile media (also referred to as volatile storage, memory, memory storage, memory circuitry, and/or similar terms used herein interchangeably). Furthermore, in an embodiment, the volatile memory 215 can include one or more volatile storage or memory media, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media can be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like can be used to control certain aspects of the operation of the segment-wise prediction machine learning computing entity 106 with the assistance of the processing element 205 and operating system.

As indicated, in one embodiment, the segment-wise prediction machine learning computing entity 106 can also include the network interface 220. In an embodiment, the network interface 220 can be one or more communications interfaces for communicating with various computing entities, such as by communicating data, content, information, and/or similar terms used herein interchangeably that can be transmitted, received, operated on, processed, displayed, stored, and/or the like. Such communication can be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the segment-wise prediction machine learning computing entity 106 can be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the segment-wise prediction machine learning computing entity 106 can include or be in communication with one or more input elements, such as a keyboard input, a mouse input, a touch screen/display input, motion input, movement input, audio input, pointing device input, joystick input, keypad input, and/or the like. The segment-wise prediction machine learning computing entity 106 can also include or be in communication with one or more output elements (not shown), such as audio output, video output, screen/display output, motion output, movement output, and/or the like.

Exemplary External Computing Entity

FIG. 3 provides an illustrative schematic representative of an external computing entity 102 that can be used in conjunction with embodiments of the present disclosure. In general, the terms device, system, computing entity, entity, and/or similar words used herein interchangeably can refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. The external computing entity 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) which provide signals to and receives signals from the transmitter 304 and receiver 306, correspondingly.

The signals provided to and received from the transmitter 304 and the receiver 306, correspondingly, can include signaling information/data in accordance with air interface standards of applicable wireless systems. In this regard, the external computing entity 102 can be capable of operating with one or more air interface standards, communication protocols, modulation types, and access types. More particularly, the external computing entity 102 can operate in accordance with any of a number of wireless communication standards and protocols, such as those described above with regard to the segment-wise prediction machine learning computing entity 106. In a particular embodiment, the external computing entity 102 can operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 can operate in accordance with multiple wired communication standards and protocols, such as those described above with regard to the segment-wise prediction machine learning computing entity 106 via a network interface 320.

Via these communication standards and protocols, the external computing entity 102 can communicate with various other entities using concepts, such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 can include location determining aspects, devices, modules, functionalities, and/or similar words used herein interchangeably. For example, the external computing entity 102 can include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites can be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 can include indoor positioning aspects, such as a location module adapted to acquire, for example, latitude, longitude, altitude, geocode, course, direction, heading, speed, time, date, and/or various other information/data. Some of the indoor systems can use various position or location technologies including RFID tags, indoor beacons or transmitters, Wi-Fi access points, cellular towers, nearby computing devices (e.g., smartphones, laptops) and/or the like. For instance, such technologies can include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 can also comprise a user interface (that can include a display 316 coupled to the processing element 308) and/or a user input interface (coupled to the processing element 308). For example, the user interface can be a user application, browser, user interface, graphical user interface, dashboard, and/or similar words used herein interchangeably executing on and/or accessible via the external computing entity 102 to interact with and/or cause display of information/data from the segment-wise prediction machine learning computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *) and other keys used for operating the external computing entity 102, and can include a full set of alphabetic keys or set of keys that can be activated to provide a full set of alphanumeric keys. In addition to providing input, the user input interface can be used, for example, to activate or deactivate certain functions, such as screen savers and/or sleep modes.

The external computing entity 102 can also include volatile memory 322 and/or non-volatile memory 324, which can be embedded and/or can be removable. For example, the non-volatile memory can be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory can be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile memory 322 and/or the non-volatile memory 324 can store databases, database instances, database management systems, data, applications, programs, program modules, scripts, source code, object code, byte code, compiled code, interpreted code, machine code, executable instructions, and/or the like to implement the functions of the external computing entity 102. As indicated, this can include a user application that is resident on the entity or accessible through a browser or other user interface for communicating with the segment-wise prediction machine learning computing entity 106 and/or various other computing entities.

In another embodiment, the external computing entity 102 can include one or more components or functionalities that are the same or similar to those of the segment-wise prediction machine learning computing entity 106, as described in greater detail above. As will be recognized, these architectures and descriptions are provided for exemplary purposes only and are not limiting to the various embodiments.

In various embodiments, the external computing entity 102 can be embodied as an artificial intelligence (AI) computing entity, such as a virtual assistant AI device, and/or the like. Accordingly, the external computing entity 102 can be configured to provide and/or receive information/data from a user via an input/output mechanism, such as a display, a camera, a speaker, a voice-activated input, and/or the like. In certain embodiments, an AI computing entity can comprise one or more predefined and executable program algorithms stored within an onboard memory storage module, and/or accessible over a network. In various embodiments, the AI computing entity can be configured to retrieve and/or execute one or more of the predefined program algorithms upon the occurrence of a predefined trigger event.

IV. EXEMPLARY SYSTEM OPERATIONS

As described below, various embodiments of the present invention introduce techniques that improve the training speed of segment-wise processing machine learning frameworks given a constant/target predictive accuracy by introducing a segment-wise processing machine learning framework architecture that comprises a text embedding machine learning model that is configured to generate a document embedding for the input segment based at least in part on the document segment for the input segment and a code embedding machine learning model that is configured to generate a code embedding for the respective predictive code for the input segment, where the segment-wise prediction machine learning framework is configured to generate the segment-wise prediction score for the input segment based at least in part on the document embedding for the input segment and the code embedding for the respective predictive code for the input segment, and the text embedding machine learning model is trained as part of a code prediction machine learning model that is configured to generate, for a particular input document data object, a selected code subset of the group of predictive codes. The combination of the noted components enables the proposed segment-wise processing machine learning framework to generate more accurate segment-wise predictions, which in turn increases the training speed of the proposed segment-wise processing machine learning framework given a constant predictive accuracy. It is well-understood in the relevant art that there is typically a tradeoff between predictive accuracy and training speed, such that it is trivial to improve training speed by reducing predictive accuracy, and thus the real challenge is to improve training speed without sacrificing predictive accuracy through innovative model architectures. See, e.g., Sun et al., *Feature-Frequency—Adaptive On-line Training for Fast and Accurate Natural Language Processing* in 40(3) Computational Linguistic 563 at Abst. ("Typically, we need to make a tradeoff between speed and accuracy. It is trivial to improve the training speed via sacrificing accuracy or to improve the accuracy via sacrificing speed. Nevertheless, it is nontrivial to improve the training speed and the accuracy at the same time"). Accordingly, techniques that improve predictive accuracy without harming training speed, such as various techniques described herein, enable improving training speed given a constant predictive accuracy. Therefore, by improving accuracy of performing segment-wise machine learning predictions, various embodiments of the present invention improve the training speed of segment-wise processing machine learning frameworks given a constant/target predictive accuracy.

In general, embodiments of the present disclosure provide methods, apparatus, systems, computing devices, computing entities, and/or the like for providing event valuation forecasting using machine learning. Certain embodiments of the systems, methods, and computer program products that facilitate recommendation prediction and/or prediction-based actions employ one or more machine learning models and/or one or more machine learning techniques.

Various embodiments of the present disclosure address technical challenges related to accurately, efficiently, and/or reliably performing predictive data analysis of data stored in disparate data sources. For example, in various embodiments, proposed solutions provide for modeling using machine learning. In various embodiments, proposed solutions disclose segment-wise prediction using machine learning. In some embodiments, one or more machine learning models to facilitate segment-wise prediction can be trained and/or generated based at least in part on the predictive code data 116, the document segment data 118, and/or the embedding data 120. After the one or more machine learning models are generated, the one or more machine learning models can be utilized to perform accurate, efficient, and reliable segment-wise predictions.

Machine Learning Techniques for Segment-Wise Modeling

FIG. 4 illustrates an example system 400 related to a text embedding machine learning model, in accordance with one or more embodiments of the present disclosure. The system 400 includes a text embedding machine learning model 402. In one or more embodiments, the modeling engine 112 can employ the text embedding machine learning model 402 to predict one or more code embeddings for a prediction input data object (e.g., for a prediction input data object that is associated with a health insurance claim). The one or more code embeddings can be, for example, one or more predicted CPT codes for the prediction input data object. For instance, the text embedding machine learning model 402 can receive input segment data 404 for the prediction input data object. The input segment data 404 can include one or more input segments (e.g., one or more claim lines) that are associated with the prediction input data object, where each input segment is associated with a distinct predictive code of a group of predictive codes for the prediction input data object. In an embodiment, an input segment can be a claim line for a medical record that is associated with a respective predictive code such as a respective CPT code. A predictive code can be, for example, a CPT code. Additionally, a document segment can be a segment of a medical record that is deemed related to the predictive code for the input segment. In various embodiments, the input segment data 404 can be associated with pre-processed text of a document such as, for example, a medical record document. In various embodiments, the input segment data 404 can be a data construct for the input segment. In certain embodiments, the input segment data 404 can be a data construct for a claim line of a medical record In various embodiments, the input segment data 404 can be generated based at least in part on pre-processing of text using UMLS text descriptions and/or page classifiers such that non-relevant text and/or irrelevant pages are removed from an unprocessed version of text. The text embedding machine learning model 402 can be configured to perform one or more machine learning operations with respect to the input segment data 404 to provide one or more predictive codes 406. The one or more predictive codes 406 can be, for example, one or more CPT predictions (e.g., one or more predicted CPT codes) for a given claim.

FIG. 5 illustrates a non-limiting embodiment of the text embedding machine learning model 402. To provide the one or more predictive codes 406, the text embedding machine learning model 402 can represent the input segment data 404 as an embedding layer 502. The text embedding machine learning model 402 can additionally employ a set of pre-trained weights from an embedding model such as, for example, a BioWord2Vec embedding model, to provide the one or more predictive codes 406. Additionally, in various embodiments, the input segment data 404 can be processed by a set of convolution layers 504, a set of pooling layers 506, a concatenate layer 508, a fully connected layer 510, and/or a Softmax layer 512 to provide the one or more predictive codes 406. The set of convolution layers 504 can be, for example, one or more convolutional layers associated with respective convolutional filters. The set of pooling layers 506 can be, for example, one or more max pooling layers.

FIG. 6 illustrates an example segment-wise prediction machine learning framework 600, in accordance with one or more embodiments of the present disclosure. The segment-wise prediction machine learning framework 600 includes a segment-wise prediction model 602. The segment-wise prediction model 602 can be configured to generate a prediction output 604 based at least in part on one or more input segment features 606 and/or one or more input document data object features 608. In one or more embodiments, the segment-wise prediction model 602 includes the text embedding machine learning model 402. In an embodiment as illustrated in FIG. 6, the text embedding machine learning model 402 can be a model version that is not trainable during training and/or deployment of the segment-wise prediction model 602. For example, in certain embodiments during an initial training stage for the segment-wise prediction model 602, the text embedding machine learning model 402 can be deployed as a pretrained machine learning model without being trained during the initial training stage. In various embodiments, a pre-trained version of the text embedding machine learning model 402 can be inserted into the segment-wise prediction model 602, and weights for the text embedding machine learning model 402 can be frozen such that the weights are not updated during training of the segment-wise prediction model 602. In various embodiments, the text embedding machine learning model 402 can generate one or more predictive codes based at least in part on a portion of the one or more input segment features 606. For example, the text embedding machine learning model 402 can generate one or more predictive codes based at least in part on one or more text features included in the one or more input segment features 606.

The segment-wise prediction model 602 can employ the one or more predictive codes generated by the text embedding machine learning model 402 to generate the prediction output 604. Additionally, the segment-wise prediction model 602 can additionally be configured to employ one or more other portions of the one or more input segment features 606 and/or the one or more input document data object features 608 to generate the prediction output 604. For example, the segment-wise prediction model 602 can employ one or more predictive code embedding features, one or more modifier features, one or more product features, one or more units features (e.g., service unit features), and/or one or more other features included in the one or more input segment features 606 to generate the prediction output 604. Additionally or alternatively, the segment-wise prediction model 602 can employ one or more case predictive code embedding features, one or more case modifier features, and/or one or more other features included in the input document data object features 608 to generate the prediction output 604. In various embodiments, the input segment can be represented as an embedding layer and the segment-wise prediction model 602 can learn one or more similarities between predictive codes that deemed to be similar to each other. The initial weights of the segment-wise prediction model 602 can also be refined during training of the segment-wise prediction model 602. Training of the segment-wise prediction model 602 can also employ one or more of the input segment features 606 and/or the input document data object feature 608. In certain embodiments, the segment-wise prediction model 602 can perform a concatenation process with respect features via concatenate 610. For example, the segment-wise prediction model 602 can concatenate the one or more predictive codes generated by the text embedding machine learning model 402, the one or more other portions of the one or more input segment features 606 and/or the one or more input document data object features 608 via concatenate 610 to generate the prediction output 604.

FIG. 7 illustrates an example segment-wise prediction machine learning framework 600', in accordance with one or more embodiments of the present disclosure. The segment-wise prediction machine learning framework 600' is an alternate embodiment of the segment-wise prediction machine learning framework 600 that includes the segment-wise prediction model 602. The segment-wise prediction model 602 can be configured to generate a prediction output 604 based at least in part on one or more input segment features 606 and/or one or more input document data object features 608. In one or more embodiments, the segment-wise prediction model 602 includes a trainable version of the text embedding machine learning model 402. For instance, in an embodiment as illustrated in FIG. 7, the text embedding machine learning model 402 can be a model version that is trainable during training and/or deployment of the segment-wise prediction model 602. For example, in certain embodiments during one or more training stages and/or one or more deployment stages for the segment-wise prediction model 602, the text embedding machine learning model 402 can be deployed as a pretrained machine learning model that is trained as part of the segment-wise prediction model 602. In various embodiments, the learning rate of the segment-wise prediction model 602 is reduced and layers of the segment-wise prediction model 602 are fine-tuned to refine the weights for both the segment-wise prediction model 602 and the text embedding machine learning model 402. For example, during the tuning of the segment-wise prediction model 602, the text embedding machine learning model 402 can be altered to an unfrozen state such that the weights for the text embedding machine learning model 402 are updated during training of the segment-wise prediction model 602. In various embodiments, the text embedding machine learning model 402 can generate one or more predictive codes based at least in part on a portion of the one or more input segment features 606. For example, the text embedding machine learning model 402 can generate one or more predictive codes based at least in part on one or more text features included in the one or more input segment features 606.

FIG. 8 illustrates an example segment-wise prediction machine learning framework 600", in accordance with one or more embodiments of the present disclosure. The segment-wise prediction machine learning framework 600" is an alternate embodiment of the segment-wise prediction machine learning framework 600 and/or the segment-wise prediction machine learning framework 600' that includes the segment-wise prediction model 602. In various embodiments, the segment-wise prediction model 602 can concatenate the one or more predictive codes generated by the text embedding machine learning model 402, the one or more other portions of the one or more input segment features 606, and/or the one or more input document data object features 608 via concatenate 610 to generate concatenated features. The concatenated features can also be further processed by a dense layer 802, a dropout layer 804, and/or a sigmoid layer 806 to generate the prediction output 604. The dense layer 802 can be, for example, a neural network layer that receives input from one or more other previous layers in the segment-wise prediction model 602. The dropout layer 804 can be a machine learning layer that randomly sets values within the dropout layer 804 to certain values and/or incrementally scales the values during training of the dropout layer 804. The sigmoid layer 806 can be a machine learning layer that applies a sigmoid function to data to, for example, compress output provided by the dense layer 802 and/or the dropout layer 804.

FIG. 9 illustrates an example machine learning system 900, in accordance with one or more embodiments of the present disclosure. The machine learning system 900 includes the text embedding machine learning model 402, the segment-wise prediction model 602, a text classification machine learning model 902, a page classification machine learning model 904, a code embedding machine learning model 944, and/or a modifier embedding machine learning model 906. In various embodiments, the text classification machine learning model 902 and/or the page classification machine learning model 904 can be deployed via a preprocess text process 901. In various embodiments, the text classification machine learning model 902 can be configured to remove non-relevant text from an input segment 910 of one or more input document data objects 912 based at least in part on a UMLS text description 914. Additionally or alternatively, in various embodiments, the page classification machine learning model 904 can be configured to remove non-relevant pages from the input segment 910 of the one or more input document data objects 912 based at least in part on page classifier data. In certain embodiments, the text classification machine learning model 902 can additionally employ one or more page classifications provided by the page classification machine learning model 904 to remove non-relevant text from the input segment 910. In certain embodiments, the one or more input document data objects 912 can be one or more medical records. Additionally, in certain embodiments, the input segment data 404 can be generated based at least in part on the one or more input document data objects 912. For example, the input segment data 404 can include claim line data associated with the one or more medical records. The input segment 910 can be, for example, one or more claim lines for the one or more medical records.

In various embodiments, a feature extraction process 903 can be performed to generate one or more features based at least in part on data associated with the text embedding machine learning model 402, the text classification machine learning model 902, the page classification machine learning model 904, the code embedding machine learning model 944, and/or the modifier embedding machine learning model 906. The one or more features associated with the feature extraction process 903 can additionally be generated based at least in part on features extracted from the input segment 910 and/or the one or more input document data objects 912. The one or more features associated with the feature extraction process 903 can include, for example, the one or more input segment feature 606 and/or the one or more input document data object features 608. In one or more embodiments, the one or more features associated with the feature extraction process 903 can include a text embedding 920, a code embedding 922, an average modifier embedding 924, an additional feature extraction 926, an average code embedding 928, an average modifier embedding 930, and/or one or more other features to provide as input to the segment-wise prediction model 602. In certain embodiments, the text embedding 920, the code embedding 922, the average modifier embedding 924, the additional feature extraction 926, the average code embedding 928, the average modifier embedding 930, and/or the one or more other features can be concatenated via the concatenate 610 to provide the features in a format suitable for processing by the segment-wise prediction model 602. For example, in certain embodiments, the text embedding 920, the code embedding 922, the average modifier embedding 924, the additional feature extraction 926, the average code embedding 928, the average modifier embedding 930, and/or the one or more other features can be converted into an input feature vector that is applied to the segment-wise prediction model 602 to generate the prediction output 604. In certain embodiments, an optimization process 950 can be performed to further optimize accuracy of the prediction output 604. In some embodiments, when the goal of the segment-wise prediction model 602 is to output the probability of a binary classification (e.g., classified as a "0" or "1", or classified as a "pay" or "deny" decision, etc.), an initial decision threshold can be set and then fine-tuned based at least in part on the optimization process 950. The finely-tuned thresholds can be employed to optimize machine learning goals and/or objectives for the segment-wise prediction model 602 such as, for example, a pay precision (e.g., how accurate the model is predicting a '1' on a claim line) and deny recall (e.g., how many denials or reviews from a set would the model find on average).

FIG. 10 illustrates an example embodiment of the optimization process 950, in accordance with one or more embodiments of the present disclosure. In various embodiments, the optimization process 950 can iterate through a set of candidate segment-wise prediction score thresholds 1002 such that respective candidate segment-wise prediction score thresholds are applied to a set of training prediction input data objects 1004. The set of candidate segment-wise prediction score thresholds 1002 can be, for example, a set of predefined thresholds. Additionally, the set of training prediction input data objects 1004 can be, for example, a training set of predictions to classify a prediction as either a first classification (e.g., classification A) or a second classification (e.g., classification B). In various embodiments, the first classification can correspond to a "pay" classification and the second classification decision can correspond to a "deny" classification decision for a medical claim. In various embodiments, the optimization process 950 can employ a set of optimization objectives 1006. The set of optimization objectives 1006 can be associated with respective optimization measures. For example, the set of optimization objectives 1006 can be associated with respective machine learning object constraints for the segment-wise prediction model 602. Additionally, for each optimization objective from the set of optimization objectives 1006, the optimization process 950 can calculate a code-specific optimization measure 1008 when applied to the training prediction input data objects 1004. The code-specific optimization measure 1008 can be, for example, an optimizing metric to optimize a decision threshold between the first classification (e.g., classification A) and the second classification (e.g., classification B). For example, the optimization process 950 can generate a set of optimized segment-wise prediction score thresholds 1012 based at least in part on the code-specific optimization measure 1008.

In a non-limiting example, a first optimization objective from the set of optimization objectives 1006 can be that a first feature for the first classification is to satisfy a first criterion and a second optimization objective from the set of optimization objectives 1006 can be that a second feature for the second classification is to satisfy a second criterion. Accordingly, the optimization process 950 can determine a set of thresholds (e.g., the set of optimized segment-wise prediction score thresholds 1012) that satisfy both the first optimization objective and the second optimization objective. Additionally, in certain embodiments, the optimization process 950 can apply the code-specific optimization measure 1008 from remaining thresholds from the set of candidate segment-wise prediction score thresholds 1002 to determine an optimal threshold for the decision threshold between the first classification (e.g., classification A) and the second classification (e.g., classification B).

In certain embodiments, the code-specific optimization measure 1008 can be configured based at least in part on an F-score metric such that the code-specific optimization measure 1008 corresponds to:

$$F3\_1/3 = \frac{F_{1/3}(\text{label} = 1) + F_3(\text{label} = 0)}{2} \qquad \text{Equation 1}$$

For example, the code-specific optimization measure 1008 can be a measure for a particular prediction score such that a particular minimum decision for the first classification and a particular maximum decision for the second classification are satisfied. In certain embodiments, the optimization process 950 can select a decision threshold with an optimal code-specific optimization measure 1008 (e.g., an optimal metric score) for the prediction output 604. In various embodiments, the optimal code-specific optimization measure 1008 can describe an inferred correlation of filtering of a code-related input subset of the plurality of training prediction input data objects that are associated with the particular predictive code with an overall optimization measure that is determined based at least in part on the one or more optimization measures.

In certain embodiments, the optimization process 950 can employ a two-step threshold calculation to determine the decision threshold with the optimal code-specific optimization measure 1008. For example, a group-specific optimization measure for the candidate segment-wise prediction score threshold 1002 can be generated. The group-specific optimization measure can describe inferred correlation of filtering of a group-related input subset of the plurality of training prediction input data objects 1004 that are associated with a code group for the particular predictive code with the overall optimization measure. Additionally, a smoothed optimization measure for the candidate segment-wise prediction score thresholds 1002 can be generated based at least in part on the code-specific optimization measure 1008 for the candidate segment-wise prediction score thresholds 1002 and the group-specific optimization measure for the candidate segment-wise prediction score thresholds 1002. Then, the segment-wise prediction score threshold from the plurality of candidate segment-wise prediction score thresholds 1002 can be selected based at least in part on each smoothed optimization measure. In certain embodiments, the optimization process 950 can employ the two-step threshold calculation with Bayesian smoothing to determine the decision threshold with the optimal code-specific optimization measure 1008. For example, after calculating the decision threshold, one or more steps of the modeling process for the segment-wise prediction model 602 can be repeated for certain types of text embeddings (e.g., certain ontology groupings in a UMLS ontology structure). Bayesian Smoothing of the two decision thresholds can then be performed to facilitate identification of predictive codes with higher volume and predictive codes with lower volume.

Accordingly, using the machine learning techniques described herein, various embodiments of the present invention introduce techniques that improve the training speed of segment-wise processing machine learning frameworks given a constant/target predictive accuracy by introducing a segment-wise processing machine learning framework architecture that comprises a text embedding machine learning model that is configured to generate a document embedding for the input segment based at least in part on the document segment for the input segment and a code embedding machine learning model that is configured to generate a code embedding for the respective predictive code for the input segment, where the segment-wise prediction machine learning framework is configured to generate the segment-wise prediction score for the input segment based at least in part on the document embedding for the input segment and the code embedding for the respective predictive code for the input segment, and the text embedding machine learning model is trained as part of a code prediction machine learning model that is configured to generate, for a particular input document data object, a selected code subset of the group of predictive codes. The combination of the noted components enables the proposed segment-wise processing machine learning framework to generate more accurate segment-wise predictions, which in turn increases the training speed of the proposed segment-wise processing machine learning framework given a constant predictive accuracy. It is well-understood in the relevant art that there is typically a tradeoff between predictive accuracy and training speed, such that it is trivial to improve training speed by reducing predictive accuracy, and thus the real challenge is to improve training speed without sacrificing predictive accuracy through innovative model architectures. See, e.g., Sun et al., *Feature-Frequency—Adaptive On-line Training for Fast and Accurate Natural Language Processing* in 40(3) Computational Linguistic 563 at Abst. ("Typically, we need to make a tradeoff between speed and accuracy. It is trivial to improve the training speed via sacrificing accuracy or to improve the accuracy via sacrificing speed. Nevertheless, it is nontrivial to improve the training speed and the accuracy at the same time"). Accordingly, techniques that improve predictive accuracy without harming training speed, such as various techniques described herein, enable improving training speed given a constant predictive accuracy. Therefore, by improving accuracy of performing segment-wise machine learning predictions, various embodiments of the present invention improve the training speed of segment-wise processing machine learning frameworks given a constant/target predictive accuracy.

Prediction-Based Actions and/or Visualizations

FIG. 11 illustrates an example system 1100 for providing prediction-based actions and/or visualizations, in accordance with one or more embodiments of the present disclosure. The system 1100 includes the prediction output 1104 provided by the segment-wise prediction model 602. In one or more embodiments, one or more prediction-based actions can be performed based at least in part on the prediction output 1104. For example, data associated with the prediction output 1104 can be stored in a storage system, such as the storage subsystem 108 or another storage system associated with the segment-wise prediction machine learning system 101. The data stored in the storage system can be employed for reporting, decision-making purposes, operations management, healthcare management, and/or other purposes. In certain embodiments, the data stored in the storage system can be employed to provide one or more insights to assist with healthcare decision making processes such as, for example, clinical decisions during a clinical review of medical records. Additionally or alternatively, the segment-wise prediction model 602 and/or one or more other machine learning models can be retrained based at least in part on one or more features associated with the prediction output 1104. For example, one or more relationships between features mapped in the segment-wise prediction model 602 and/or one or more other machine learning models can be adjusted (e.g., refitted) based at least in part on data associated with the prediction output 1104. In another example, cross-validation, hyperparameter optimization, and/or regularization associated with the segment-wise prediction model 602 and/or one or more other machine learning models can be adjusted based at least in part on one or more features associated with the prediction output 1104. Additionally or alternatively, a visualization 1106 can be generated based at least in part on the prediction output 1104. The visualization 1106 can include, for example, one or more graphical elements for an electronic interface (e.g., an electronic interface of a user device) based at least in part on the prediction output 1104.

It is to be appreciated that the prediction output 604 can additionally or alternatively be employed for a number of additional applications. For example, Clinical Decision Support (CDS), Clinical Decisions for Fraud (CDF), automatic claim creation, and/or efficient auditing of payment integrity clinical review decisions can be integrated into the visualization 1106. Accordingly, the prediction output 604 can be employed to improve efficiency and/or reduce waste in an adjudication process related to medical records. The prediction output 604 can also assist clinical reviewers with review of medical records by presenting relevant pages, as calculated by the prediction output 604 for each claim line. In certain embodiments, the visualization 1106 can include visual indicators (e.g., highlights) to indicate insights related to classification decisions (e.g., pay or deny decisions), as provided by the segment-wise prediction model 602. Additionally or alternatively, the prediction output 604 can be employed to identify potential issues and/or certain content within medical records, thus reducing a number of computing resources. Furthermore, the prediction output 604 can additionally or alternatively be employed to identify particular types of decisions by leveraging predicted qualities for different predictive codes with respect to classification decisions. In some embodiments, the visualization 1106 can provide a clinical decision support user interface tool related to improve clinical review of medical records.

FIG. 12 illustrates an example user interface 1200 for providing prediction-based visualizations, in accordance with one or more embodiments of the present disclosure. The user interface 1200 can be, for example, an electronic interface (e.g., a graphical user interface) of the external computing entity 102. In various embodiments, the user interface 1200 can be provided via the display 316 of the external computing entity 102. The user interface 1200 can be configured to render the visualization 1106. In various embodiments, the visualization 1106 can provide a visualization of a predictive output (i.e., one or more pay/denial predictions) for a set of claim lines of a claim of a medical record. For example, the visualization 1106 can render one or more visual elements related to a predictive output (i.e., one or more pay/denial predictions) for a set of claim lines of a claim of a medical record. Additionally, in certain embodiments, the user interface 1200 can be configured to render claim data 1202 related to the visualization 1106. The claim data 1202 can provide textual information and/or visual information related to one or more claims (e.g., one or more claim lines) of one or more claims of a medical record. In various embodiments, the user interface 1200 can be configured as a user interface (e.g., a clinical decision support user interface) for clinical decision automation related to medical records.

Another operational example of prediction-based actions that may be performed based at least in part on predictive outputs comprise performing operational load balancing for post-prediction systems that perform post-prediction operations (e.g., automated specialist appointment scheduling operations) based at least in part on segment-wise predictive outputs. For example, in some embodiments, a predictive recommendation computing entity determines D classifications for D prediction input data objects based at least in part whether the selected region subset for each prediction input data object as generated by the predictive recommendation model comprises a target region (e.g., a target brain region). Then, the count of D prediction input data objects that are associated with an affirmative classification, along with a resource utilization ratio for each prediction input data object, can be used to predict a predicted number of computing entities needed to perform post-prediction processing operations with respect to the D prediction input data objects. For example, in some embodiments, the number of computing entities needed to perform post-prediction processing operations (e.g., automated specialist scheduling operations) with respect to D prediction input data objects can be determined based at least in part on the output of the equation: $R = \text{ceil}(\Sigma_k^{k=K} ur_k)$, where R is the predicted number of computing entities needed to perform post-prediction processing operations with respect to the D prediction input data objects, cello) is a ceiling function that returns the closest integer that is greater than or equal to the value provided as the input parameter of the ceiling function, k is an index variable that iterates over K prediction input data objects among the D prediction input data objects that are associated with affirmative classifications, and $ur_k$ is the estimated resource utilization ratio for a kth prediction input data object that may be determined based at least in part on a patient history complexity of a patient associated with the prediction input data object. In some embodiments, once R is generated, a predictive recommendation computing entity can use R to perform operational load balancing for a server system that is configured to perform post-prediction processing operations with respect to D prediction input data objects. This may be done by allocating computing entities to the post-prediction processing operations if the number of currently-allocated computing entities is below R, and deallocating currently-allocated computing entities if the number of currently-allocated computing entities is above R.

Generating a Prediction Output for a Prediction Input Data Object Using Machine Learning FIG. 13 is a flowchart diagram of an example process 1300 for generating a prediction output for a prediction input data object that is associated with a plurality of input segments, in accordance with one or more embodiments of the present disclosure. Via the various steps/operations of process 1300, the segment-wise prediction machine learning computing entity 106 can process the predictive code data 116, the document segment data 118, the embedding data 120, and/or other data using one or more artificial intelligence techniques (e.g., one or more machine learning techniques) to provide improved prediction output. In certain embodiments, via the various steps/operations of process 1300, the segment-wise prediction machine learning computing entity 106 can additionally or alternatively process the text embedding 920, the code embedding 922, the average modifier embedding 924, the additional feature extraction 926, the average code embedding 928, the average modifier embedding 930, and/or the one or more other features using one or more artificial intelligence techniques (e.g., one or more machine learning techniques) to provide improved prediction output. In doing so, the segment-wise prediction machine learning computing entity 106 can utilize machine learning solutions to infer important predictive insights and/or inferences related to data and/or features associated with one or more input document data objects such as, for example, the one or more input document data objects 912.

The process 1300 begins at step/operation 1302 when the text processing engine 109 of the segment-wise prediction machine learning computing entity 106 identifies a group of predictive codes, where each input segment is associated with a respective predictive code of the group of predictive codes. The predictive codes can be, for example, CPT codes associated with a claim line of a medical record.

At step/operation 1304, the text processing engine 109 of the segment-wise prediction machine learning computing entity 106 generates a document segment of an input document data object for the prediction input data object that is associated with the input segment, wherein the document segment is determined to be related to the respective predictive code for the input segment.

In certain embodiments, generating the document segment for a particular input segment comprises identifying a plurality of input pages of the input document data object. In certain embodiments, generating the document segment for a particular input segment additionally comprises, for each input page, generating, using a page classification machine learning model and based at least in part on the input page, a page relevance classification score. In certain embodiments, generating the document segment for a particular input segment additionally comprises determining a relevant page subset of the plurality of input pages based at least in part on each page relevance classification score. In certain embodiments, generating the document segment for a particular input segment additionally comprises, for each relevant page in the relevant page subset, determining a referential similarity score based at least in part on the relevant page and a reference document data object for the respective predictive code that is associated with the particular input segment. In certain embodiments, generating the document segment for a particular input segment additionally comprises generating the document segment based at least in part on each referential similarity score.

At step/operation 1306, the modeling engine 112 of the segment-wise prediction machine learning computing entity 106 generates, using a segment-wise prediction machine learning framework, and based at least in part on the document segment for the input segment and the respective predictive code for the input segment, a segment-wise prediction score for the input segment, where: (i) the segment-wise prediction machine learning framework comprises a text embedding machine learning model that is configured to generate a document embedding for the input segment based at least in part on the document segment for the input segment and a code embedding machine learning model that is configured to generate a code embedding for the respective predictive code for the input segment, (ii) the segment-wise prediction machine learning framework is configured to generate the segment-wise prediction score for the input segment based at least in part on the document embedding for the input segment and the code embedding for the respective predictive code for the input segment, and/or (iii) the text embedding machine learning model is trained as part of a code prediction machine learning model that is configured to generate, for a particular input document data object, a selected code subset of the group of predictive codes.

In various embodiments, generating the code embedding machine learning model comprises identifying one or more training prediction input data objects. In various embodiments, generating the code embedding machine learning model additionally comprises generating a code occurrence document data object that describes predictive code co-occurrences in a training prediction input data object using a respective sentence of the code occurrence document data object. In various embodiments, generating the code embedding machine learning model additionally comprises generating the code embedding machine learning model using one or more language modeling tasks that are defined in accordance with the code occurrence document data object.

In various embodiments, the segment-wise prediction machine learning framework is configured to generate the segment-wise prediction score for a particular input segment based at least in part on a code embedding distribution measure of each code embedding that is associated with a subset of the group of predictive codes that are associated with the plurality of input segments.

In various embodiments, during an initial training stage of the segment-wise prediction machine learning framework, the text embedding machine learning model is deployed as a pretrained machine learning model without being trained during the initial training stage.

In various embodiments, during a subsequent training stage of the segment-wise prediction machine learning framework, the text embedding machine learning model is deployed as a pretrained machine learning model that is trained as part of the segment-wise prediction machine learning framework.

At step/operation 1308, the modeling engine 112 of the segment-wise prediction machine learning computing entity 106 generates, based at least in part on each segment-wise prediction score, the prediction output. In certain embodiments, the prediction output indicates whether a claim line for a medical record is to be paid or denied.

In various embodiments, generating the predictive output comprises, for each input segment, generating a segment-wise classification based at least in part on whether the segment-wise prediction score for the input segment satisfies a segment-wise prediction score threshold for the respective predictive code that is associated with the input segment. In various embodiments, generating the predictive output additionally comprises generating the predictive output based at least in part on each segment-wise classification.

In various embodiments, generating the segment-wise prediction score threshold for a particular predictive code comprises, during training of the segment-wise prediction machine learning framework based at least in part on a plurality of training prediction input data objects, identifying a plurality of candidate segment-wise prediction score thresholds that satisfy one or more defined optimization objectives that are associated with one or more optimization measures. In various embodiments, for each candidate segment-wise prediction score threshold, a code-specific optimization measure for the candidate segment-wise prediction score threshold can be generated. The code-specific optimization measure can describe inferred correlation of filtering a code-related input subset of the plurality of training prediction input data objects that are associated with the particular predictive code with an overall optimization measure that is determined based at least in part on the one or more optimization measures. In various embodiments, a group-specific optimization measure for the candidate segment-wise prediction score threshold can be generated. The group-specific optimization measure can describe inferred correlation of filtering a group-related input subset of the plurality of training prediction input data objects that are associated with a code group for the particular predictive code with the overall optimization measure. In various embodiments, a smoothed optimization measure for the candidate segment-wise prediction score threshold can be generated based at least in part on the code-specific optimization measure for the candidate segment-wise prediction score threshold and the group-specific optimization measure for the candidate segment-wise prediction score threshold. In various embodiments, the segment-wise prediction score threshold from the plurality of candidate segment-wise prediction score thresholds can be selected based at least in part on each smoothed optimization measure.

At step/operation 1308, the modeling engine 112 of the segment-wise prediction machine learning computing entity 106 performs one or more prediction-based actions based at least in part on the prediction output. In certain embodiments, one or more graphical elements for an electronic interface are generated based at least in part on the prediction output. In certain embodiments, one or more machine learning models (e.g., text embedding machine learning model, code embedding machine learning model, code prediction machine learning model, segment-wise prediction machine learning model, etc.) can be retrained based at least in part on the prediction output.

In various embodiments, the step/operation 1304, the step/operation 1306, the step/operation 1308, and/or the step/operation 1310 can be repeated for each input segment.

Accordingly, as described above, various embodiments of the present invention introduce techniques that improve the training speed of segment-wise processing machine learning frameworks given a constant/target predictive accuracy by introducing a segment-wise processing machine learning framework architecture that comprises a text embedding machine learning model that is configured to generate a document embedding for the input segment based at least in part on the document segment for the input segment and a code embedding machine learning model that is configured to generate a code embedding for the respective predictive code for the input segment, where the segment-wise prediction machine learning framework is configured to generate the segment-wise prediction score for the input segment based at least in part on the document embedding for the input segment and the code embedding for the respective predictive code for the input segment, and the text embedding machine learning model is trained as part of a code prediction machine learning model that is configured to generate, for a particular input document data object, a selected code subset of the group of predictive codes. The combination of the noted components enables the proposed segment-wise processing machine learning framework to generate more accurate segment-wise predictions, which in turn increases the training speed of the proposed segment-wise processing machine learning framework given a constant predictive accuracy. It is well-understood in the relevant art that there is typically a tradeoff between predictive accuracy and training speed, such that it is trivial to improve training speed by reducing predictive accuracy, and thus the real challenge is to improve training speed without sacrificing predictive accuracy through innovative model architectures. See, e.g., Sun et al., *Feature-Frequency—Adaptive On-line Training for Fast and Accurate Natural Language Processing* in 40(3) Computational Linguistic 563 at Abst. ("Typically, we need to make a tradeoff between speed and accuracy. It is trivial to improve the training speed via sacrificing accuracy or to improve the accuracy via sacrificing speed. Nevertheless, it is nontrivial to improve the training speed and the accuracy at the same time"). Accordingly, techniques that improve predictive accuracy without harming training speed, such as various techniques described herein, enable improving training speed given a constant predictive accuracy. Therefore, by improving accuracy of performing segment-wise machine learning predictions, various embodiments of the present invention improve the training speed of segment-wise processing machine learning frameworks given a constant/target predictive accuracy.

V. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
   identifying, by one or more processors, a group of predictive codes corresponding to a plurality of input segments associated with a prediction input data object, wherein the group of predictive codes is from a plurality of predictive codes;
   generating, by the one or more processors, a document segment for the group of predictive codes based at least in part on an input document data object for the prediction input data object;
   generating, by the one or more processors and using a segment-wise prediction machine learning framework, a segment-wise prediction score for an input segment of the plurality of input segments based at least in part on a code embedding distribution measure of a respective code embedding that is associated with a respective predictive code of a subset of the group of predictive codes that are associated with the plurality of input segments, wherein:
   (i) the segment-wise prediction machine learning framework comprises (a) a text embedding machine learning model that is configured to generate a document embedding based at least in part on the document segment and (b) a code embedding machine learning model that is configured to generate the respective code embedding,
   (ii) the segment-wise prediction machine learning framework is configured to generate the segment-wise prediction score for the input segment based at least in part on the document embedding for the input segment and the respective code embedding for the respective predictive code, and
   (iii) the text embedding machine learning model is pretrained as part of a code prediction machine learning model that is configured to generate, for the input document data object, the subset of the group of predictive codes from the plurality of predictive codes based at least in part on the input document data object;
   generating, by the one or more processors and based at least in part on the segment-wise prediction score, a prediction output; and
   initiating, by the one or more processors, the performance of one or more prediction-based actions based at least in part on the prediction output.

2. The computer-implemented method of claim 1, wherein generating the document segment comprises:
   identifying a plurality of input pages of the input document data object;
   generating, using a page classification machine learning model a plurality of page relevance classification scores for the plurality of input pages;
   determining a relevant page subset of the plurality of input pages based at least in part on the plurality of page relevance classification scores;
   determining a referential similarity score for a relevant page in the relevant page subset based at least in part on a comparison between the relevant page and a reference document data object corresponding to the respective predictive code; and
   generating the document segment based at least in part on the referential similarity score.

3. The computer-implemented method of claim 1, wherein generating the code embedding machine learning model comprises:
  identifying one or more training prediction input data objects;
  generating a code occurrence document data object that describes a plurality of predictive code co-occurrences in a training prediction input data object using a respective sentence of the code occurrence document data object; and
  generating the code embedding machine learning model using one or more language modeling tasks that are defined in accordance with the code occurrence document data object.

4. The computer-implemented method of claim 1, wherein the segment-wise prediction machine learning framework is configured to generate the segment-wise prediction score for the input segment based at least in part on the code embedding distribution measure of each of a plurality of code embeddings that respectively correspond to the group of predictive codes that are associated with the plurality of input segments.

5. The computer-implemented method of claim 1, wherein, during an initial training stage of the segment-wise prediction machine learning framework, the text embedding machine learning model is deployed as a pretrained machine learning model without being trained during the initial training stage.

6. The computer-implemented method of claim 1, wherein, during a subsequent training stage of the segment-wise prediction machine learning framework, the text embedding machine learning model is deployed as a pretrained machine learning model that is trained as part of the segment-wise prediction machine learning framework.

7. The computer-implemented method of claim 1, wherein generating the prediction output comprises:
  generating a segment-wise classification based at least in part on whether the segment-wise prediction score for the input segment satisfies a segment-wise prediction score threshold for the respective predictive code that is associated with the input segment, and
  generating the prediction output based at least in part on the segment-wise classification.

8. The computer-implemented method of claim 7, wherein generating the segment-wise prediction score threshold comprises, during training of the segment-wise prediction machine learning framework based at least in part on a plurality of training prediction input data objects:
  identifying a plurality of candidate segment-wise prediction score thresholds that satisfy one or more defined optimization objectives that are associated with one or more optimization measures;
  generating a code-specific optimization measure for a candidate segment-wise prediction score threshold of the plurality of candidate segment-wise prediction score thresholds that describes a first inferred correlation of filtering a code-related input subset of the plurality of training prediction input data objects that are associated with the respective predictive code with an overall optimization measure that is determined based at least in part on the one or more optimization measures,
  generating a group-specific optimization measure for the candidate segment-wise prediction score threshold that describes a second inferred correlation of filtering a group-related input subset of the plurality of training prediction input data objects that are associated with a code group for the respective predictive code with the overall optimization measure,
  generating a smoothed optimization measure for the candidate segment-wise prediction score threshold based at least in part on the code-specific optimization measure and the group-specific optimization measure; and
  selecting the candidate segment-wise prediction score threshold from the plurality of candidate segment-wise prediction score thresholds based at least in part on the smoothed optimization measure.

9. A system comprising memory and one or more processors communicatively coupled to the memory, the one or more processors configured to:
  identify a group of predictive codes corresponding to a plurality of input segments associated with a prediction input data object, wherein the group of predictive codes is from a plurality of predictive codes;
  generate a document segment for the group of predictive codes based at least in part on an input document data object for the prediction input data object;
  generate, using a segment-wise prediction machine learning framework, a segment-wise prediction score for an input segment of the plurality of input segments based at least in part on a code embedding distribution measure of a respective code embedding that is associated with a respective predictive code of a subset of the group of predictive codes that are associated with the plurality of input segments, wherein:
    (i) the segment-wise prediction machine learning framework comprises (a) a text embedding machine learning model that is configured to generate a document embedding based at least in part on the document segment and (b) a code embedding machine learning model that is configured to generate the respective code embedding,
    (ii) the segment-wise prediction machine learning framework is configured to generate the segment-wise prediction score for the input segment based at least in part on the document embedding for the input segment and the respective code embedding for the respective predictive code,
    (iii) the text embedding machine learning model is pretrained as part of a code prediction machine learning model that is configured to generate, for the input document data object, the subset of the group of predictive codes from the plurality of predictive codes based at least in part on the input document data object;
  generate, based at least in part on the segment-wise prediction score, a prediction output; and
  initiate the performance of one or more prediction-based actions based at least in part on the prediction output.

10. The system of claim 9, wherein the one or more processors are further configured to:
  identify a plurality of input pages of the input document data object;
  generate, using a page classification machine learning model a plurality of page relevance classification scores for the plurality of input pages;
  determine a relevant page subset of the plurality of input pages based at least in part on the plurality of page relevance classification scores;
  determine a referential similarity score for a relevant page in the relevant page subset based at least in part on a comparison between the relevant page and a reference document data object corresponding to the-respective predictive code; and generate the document segment based at least in part on the referential similarity score.

11. The system of claim 9, wherein the one or more processors are further configured to:
identify one or more training prediction input data objects;
generate a code occurrence document data object that describes a plurality of predictive code co-occurrences in a training prediction input data object using a respective sentence of the code occurrence document data object; and
generate the code embedding machine learning model using one or more language modeling tasks that are defined in accordance with the code occurrence document data object.

12. The system of claim 9, wherein, during an initial training stage of the segment-wise prediction machine learning framework, the text embedding machine learning model is deployed as a pretrained machine learning model without being trained during the initial training stage.

13. The system of claim 9, wherein, during a subsequent training stage of the segment-wise prediction machine learning framework, the text embedding machine learning model is deployed as a pretrained machine learning model that is trained as part of the segment-wise prediction machine learning framework.

14. The system of claim 9, wherein the one or more processors are further configured to:
generate a segment-wise classification based at least in part on whether the segment-wise prediction score for the input segment satisfies a segment-wise prediction score threshold for the respective predictive code that is associated with the input segment, and
generate the prediction output based at least in part on the segment-wise classification.

15. The system of claim 14, wherein during training of the segment-wise prediction machine learning framework based at least in part on a plurality of training prediction input data objects, the one or more processors are further configured to:
identify a plurality of candidate segment-wise prediction score thresholds that satisfy one or more defined optimization objectives that are associated with one or more optimization measures;
generate a code-specific optimization measure for a candidate segment-wise prediction score threshold of the plurality of candidate segment-wise prediction score thresholds that describes a first inferred correlation of filtering a code-related input subset of the plurality of training prediction input data objects that are associated with the respective predictive code with an overall optimization measure that is determined based at least in part on the one or more optimization measures,
generate a group-specific optimization measure for the candidate segment-wise prediction score threshold that describes a second inferred correlation of filtering a group-related input subset of the plurality of training prediction input data objects that are associated with a code group for the respective predictive code with the overall optimization measure,
generate a smoothed optimization measure for the candidate segment-wise prediction score threshold based at least in part on the code-specific optimization measure and the group-specific optimization measure; and
select the candidate segment-wise prediction score threshold from the plurality of candidate segment-wise prediction score thresholds based at least in part on the smoothed optimization measure.

16. One or more non-transitory computer-readable storage media including instructions that, when executed by one or more processors, cause the one or more processors to:
identify a group of predictive codes corresponding to a plurality of input segments associated with a prediction input data object, wherein the group of predictive codes is from a plurality of predictive codes;
generate a document segment for the group of predictive codes based at least in part on an input document data object for the prediction input data object;
generate, using a segment-wise prediction machine learning framework, a segment-wise prediction score for an input segment of the plurality of input segments based at least in part on a code embedding distribution measure of a respective code embedding that is associated with a respective predictive code of a subset of the group of predictive codes that are associated with the plurality of input segments, wherein:
(i) the segment-wise prediction machine learning framework comprises (a) a text embedding machine learning model that is configured to generate a document embedding based at least in part on the document segment and (b) a code embedding machine learning model that is configured to generate the respective code embedding,
(ii) the segment-wise prediction machine learning framework is configured to generate the segment-wise prediction score for the input segment based at least in part on the document embedding for the input segment and the respective code embedding for the respective predictive code, and
(iii) the text embedding machine learning model is pretrained as part of a code prediction machine learning model that is configured to generate, for the input document data object, the subset of the group of predictive codes from the plurality of predictive codes based at least in part on the input document data object;
generate, based at least in part on the segment-wise prediction score, a prediction output; and
initiate the performance of one or more prediction-based actions based at least in part on the prediction output.

17. The one or more non-transitory computer-readable storage media of claim 16, wherein the one or more processors are further configured to:
identify a plurality of input pages of the input document data object;
generate, using a page classification machine learning model a plurality of page relevance classification scores for the plurality of input pages;
determine a relevant page subset of the plurality of input pages based at least in part on the plurality of page relevance classification scores;
determine a referential similarity score for a relevant page in the relevant page subset based at least in part on a comparison between the relevant page and a reference document data object corresponding to the respective predictive code; and
generate the document segment based at least in part on the referential similarity score.

18. The one or more non-transitory computer-readable storage media of claim 16, wherein the one or more processors are further configured to:
identify one or more training prediction input data objects;
generate a code occurrence document data object that describes a plurality of predictive code co-occurrences in a training prediction input data object using a respective sentence of the code occurrence document data object; and generate the code embedding machine learning model using one or more language modeling tasks that are defined in accordance with the code occurrence document data object.

19. The one or more non-transitory computer-readable storage media of claim 16, wherein, during an initial training stage of the segment-wise prediction machine learning framework, the text embedding machine learning model is deployed as a pretrained machine learning model without being trained during the initial training stage.

20. The one or more non-transitory computer-readable storage media of claim 16, wherein, during a subsequent training stage of the segment-wise prediction machine learning framework, the text embedding machine learning model is deployed as a pretrained machine learning model that is trained as part of the segment-wise prediction machine learning framework.

* * * * *

UNITED STATES PATENT AND TRADEMARK OFFICE
CERTIFICATE OF CORRECTION

PATENT NO. : 12,160,609 B2
APPLICATION NO. : 17/805340
DATED : December 3, 2024
INVENTOR(S) : Colum Foley et al.

Page 1 of 1

It is certified that error appears in the above-identified patent and that said Letters Patent is hereby corrected as shown below:

In the Claims

In Column 34, Line 56, Claim 2, delete "model" and insert -- model, --, therefor.

In Column 36, Line 41, Claim 9, delete "code," and insert -- code, and --, therefor.

In Column 36, Line 58, Claim 10, delete "model" and insert -- model, --, therefor.

In Column 36, Line 66, Claim 10, delete "the-respective" and insert -- the respective --, therefor.

In Column 37, Line 39, Claim 15, delete "configured to;" and insert -- configured to: --, therefor.

In Column 38, Line 49, Claim 17, delete "model" and insert -- model, --, therefor.

Signed and Sealed this
Twenty-fifth Day of February, 2025

Coke Morgan Stewart
*Acting Director of the United States Patent and Trademark Office*